United States Patent [19]

Kanehira et al.

[11] Patent Number: 5,428,056

[45] Date of Patent: Jun. 27, 1995

[54] TERPENE AMINO ALCOHOLS AND MEDICINAL USES THEREOF

[75] Inventors: Koichi Kanehira, Kurashiki; Katsushi Eziri, Okayama; Manzo Shiono; Yoshiji Fujita, both of Kurashiki; Johji Yamahara, Otsu, all of Japan

[73] Assignee: Kuraray Co., Ltd., Kurashiki, Japan

[21] Appl. No.: 151,039

[22] Filed: Nov. 12, 1993

Related U.S. Application Data

[62] Division of Ser. No. 894,567, Jun. 5, 1992, Pat. No. 5,284,850, which is a division of Ser. No. 533,395, Jun. 4, 1990, Pat. No. 5,143,921, which is a division of Ser. No. 887,431, Jul. 21, 1986, Pat. No. 4,946,847.

[30] Foreign Application Priority Data

Jul. 19, 1985 [JP] Japan ................. 60-160782
Mar. 7, 1986 [JP] Japan ................. 61-50784
Apr. 11, 1986 [JP] Japan ................. 61-84822

[51] Int. Cl.$^6$ ................. A61K 31/40; C07D 207/06
[52] U.S. Cl. ................. 514/428; 548/574
[58] Field of Search ................. 548/574; 514/428

[56] References Cited

U.S. PATENT DOCUMENTS

| | | | |
|---|---|---|---|
| 3,755,411 | 8/1973 | Henrick et al. | 260/465.6 |
| 3,873,566 | 3/1975 | Scribner | 548/367 |
| 4,151,357 | 4/1979 | Mishima et al. | 544/386 |
| 4,199,519 | 4/1980 | Mishima et al. | 544/377 X |
| 4,204,068 | 5/1980 | Caldwell et al. | 548/253 X |
| 4,586,947 | 5/1986 | Crowley et al. | 71/76 |
| 4,747,869 | 5/1988 | Kramer et al. | 71/92 |
| 4,754,043 | 7/1988 | Kreft, III et al. | 548/203 X |
| 4,935,426 | 6/1990 | Zipplies et al. | 514/255 |

FOREIGN PATENT DOCUMENTS

| | | |
|---|---|---|
| 0033432 | 8/1981 | European Pat. Off. . |
| 2348907 | 11/1977 | France . |
| 1403851 | 8/1975 | United Kingdom . |
| 2088355 | 6/1982 | United Kingdom . |

OTHER PUBLICATIONS

*Chemical Abstracts*, 93(19), 186353r, 1980, Caldwell et al.
*Chemical Abstracts*, 94(1), 3790j, 1981, Scribner.
*Chemical Abstracts*, 97(19), 163498k, 1982, Cassidy.
*Chemical Abstracts*, 100(25), 209458h, 1984, Bermudez.
*Chemical Abstracts*, 97(15), 127837m, 1982, Akutagawa et al.
*Chemical Abstracts*, 106(17), 131715s, 1987, Kanehira et al.
*Chemical Abstracts*, 97(23), 198413f, 1982, Akatuagawa et al.
*Chemical Abstracts*, 95(3), 25331h, 1981, Takasago Perfumery Co.
*Chemical Abstracts*, 102(11), 95645a, 1985, Nihon Nohyaku Co., Ltd.
*Helvetica Chimica Acta*, vol. 48, No. 1, Feb. 1, 1965, pp. 182–189, Ohloff et al.

*Primary Examiner*—Mary C. Lee
*Assistant Examiner*—Jacqueline Haley
*Attorney, Agent, or Firm*—Burns, Doane, Swecker & Mathis

[57] ABSTRACT

Novel terpene amino alcohols having an antiallergic activity or an activity of improving cerebral function are provided. Also provided are medicinal uses of the alcohols.

12 Claims, No Drawings

TERPENE AMINO ALCOHOLS AND MEDICINAL USES THEREOF

This application is a divisional of application Ser. No. 07/894,567, filed Jun. 5 1992, now U.S. Pat. No. 5,284,850, which is a divisional of U.S. Ser. No. 07/533,395, filed Jun. 4, 1990, now U.S. Pat. No. 5,143,921, which is in turn a divisional of application Ser. No. 06/887,431, filed Jul. 21, 1986, now U.S. Pat. No. 4,946,847.

BACKGROUND OF THE INVENTION

1. Field of Invention

The present invention relates to terpene amino alcohols or their pharmacologically acceptable esters or salts, and medicinal uses thereof as antiallergic agents and agents for improving cerebral function.

2. Description of the Prior Art

The living body shows various defense responses to a bacterial or viral infection or to an invading heterologous protein or drug. By these immune reactions is maintained the biological integrity of the living body. However, all immune reactions are not favorable to the living body but some reactions known as allergic reactions, are harmful to the body. At the site where allergic inflammation occurs, an antigen-antibody reaction occurs on the surface of mast cells or basophils, resulting in degranulation followed by the liberation or release of chemical transmitters such as histamine, serotonin, SRS-A, ECF-A and prostaglandin. These chemical transmitters act on many vascular systems to evoke symptoms of acute circulatory insufficiency, such as hypotension, feeble pulse, disturbance of consciousness, skin pallor, cyanosis and cold sweating, respiratory symptoms such as edema glottidis, airway constriction, wheeze due to increased mucus secretion and dyspnea. In addition, they cause gastrointestinal symptoms, such as abdominal pain, borborygmus, diarrhea and vomiting, and cutaneous symptoms such as urticaria, and in severe cases, death from shock. Studies have been conducted on compounds which inhibit the release of chemical transmitters, and consequently, disodium cromoglicate, tranilast, ketotifen, etc. have been found to act on the double lipid layer of cell membrane to decrease its fluidity and stabilize the cell membrane, thereby inhibiting release of chemical transmitters from the cell surface, and have come into use as antiallergic drugs. Terpene compounds are known to have a stabilizing activity of cell membrane, and iproheptine hydrochloride, a terpene amine, has been used as an antiallergic agent in injectable form.

The above-mentioned disodium cromoglicate does not produce an antiallergic effect when administered by the oral route, which is the most convenient route of administration. Tranilast causes cystitis-like symptoms such as hematuria, pyuria and dysuria. Ketotifen is a drug of the delayed effect type, i.e. a drug whose antiallergic effect manifests itself only after about 4-6 weeks, and moreover, it causes side effects such as drowsiness. Thus, each of these inhibitors of the release of chemical transmitter has some or other undesirable features. Iproheptine hydrochloride is known to have side effects such as drowsiness and nausea. Under the circumstances, there is awaited an improved antiallergic drug that is low in toxicity with few side effects and administrable orally on a long-term basis.

With the recent increase in the number of elderly people, various geriatric diseases have come into prominence and a need for effective countermeasures has been keenly felt. Particularly, measures against senile dementia are considered to be of great importance and much research and development work has been in progress. Recently, agents for improving cerebral circulation and metabolism such as calcium hopantenate and dihydroergotoxine mesilate have been clinically used and certain nootropic drugs such as pramiracetam have also been developed.

The above-mentioned agents for improving cerebral circulation and metabolism and nootropic agents are not sufficiently effective and some of them are toxicologically undesirable. Therefore, the development of a safe drug having an excellent activity of improving cerebral function is awaited.

It is an object of the present invention to provide novel pharmacologically active compounds.

It is another object of the present invention to provide novel compounds which display excellent and sustained antiallergic activity and are safe.

It is a further object of the present invention to provide novel compounds which are readily transferred into the brain to exhibit excellent effects of improving cerebral function and are safe.

It is still another object of the present invention to provide medicinal or pharmaceutical uses of said compounds as antiallergic agents or agents for improving cerebral function.

These objects as well as other objects and advantages of the present invention will become apparent to those skilled in the art from the following detailed description.

SUMMARY OF THE INVENTION

The present invention provides a terpene amino alcohol of the general formula $$CH_3-\underset{\underset{X^1}{|}}{\overset{\overset{CH_3}{|}}{C}}-CHCH_2(CH_2\underset{\underset{X^2}{|}}{\overset{\overset{CH_3}{|}}{C}}-CHCH_2)_n-CH_2\underset{\underset{X^3}{|}}{\overset{\overset{CH_3}{|}}{C}}-CHCH_2-Q^2 \quad (I)$$
$$\phantom{CH_3-C-CHCH_2}Y^1 \phantom{CH_2C-CHCH} Y^2 \phantom{CH_2C-CHCH} Q^1$$

wherein $X^1$ is a hydrogen atom or a hydroxyl group and $Y^1$ is a hydrogen atom or $X^1$ and $Y^1$ taken together represent a bond; $X^2$ is a hydrogen atom or a hydroxyl group and $Y^2$ is a hydrogen atom or $X^2$ and $Y^2$ taken together represent a bond; $Q^1$ and $Q^2$ are such that either one is $Y^3$ with the other being

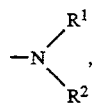

and $X^3$ is a hydrogen atom or a hydroxyl group; $Y^3$ means a hydroxyl group when $X^3$ is a hydrogen atom, or means a hydrogen atom or a hydroxyl group when $X^3$ is a hydroxyl group; $R^1$ and $R^2$ may be the same or different and each is a hydrogen atom, a lower alkyl group which may be substituted, an aryl group which may be substituted, a 4-piperidinyl group which may be substituted, pyridyl, pyridyl carbonyl or isoquinolyl group, or $R^1$ and $R^2$ taken together with the adjacent nitrogen atom forms a five- or six-membered heterocycle which may have, within the ring, 1 to 3 members selected from the group consisting of

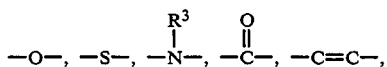

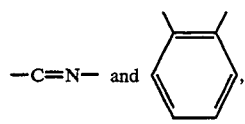

where $R^3$ means a hydrogen atom, a lower alkyl group which may be substituted or an aryl group which may be substituted; $\underline{n}$ means an integer of 0 to 2, or a pharmacologically acceptable ester or salt thereof [hereinafter, these compounds are sometimes referred to collectively as the terpene amino alcohol (I)].

The present invention in another aspect provides drugs and pharmaceutical compositions containing said terpene amino alcohol (I) as an active component.

DETAILED DESCRIPTION OF THE INVENTION

Referring to $R^1$ and $R^2$ in the above general formula (I), said lower alkyl group which may be substituted may for example be methyl, ethyl, propyl, butyl or the like, which may be substituted by hydroxyl, morpholino, phenyl or pyridyl, for instance; said aryl group which may be substituted may for example be phenyl, 4-hydroxyphenyl, 2-methoxyphenyl, 3,4,5-trimethoxyphenyl, or naphthyl; and said 4-piperidinyl group which may be substituted may for example be 4-piperidinyl, N-methyl-4-piperidinyl, or N-benzyl-4-piperidinyl. The five- or six-membered heterocyclic group that is formed by $R^1$ and $R^2$ taken together with the adjacent nitrogen atom may for example be

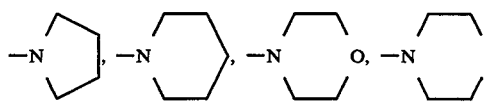

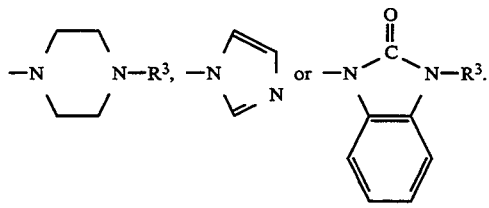

Referring to $R^3$, said lower alkyl group which may be substituted may for example be methyl, ethyl, propyl, butyl, diphenylmethyl, 2-methoxybenzyl, 3,4,5-trimethoxybenzyl, etc., and said aryl group which may be substituted may for example be phenyl, 4-hydroxyphenyl, 2-methoxyphenyl, 2,3,4-trimethoxyphenyl, naphthyl, etc.

The following is a partial listing of terpene amino alcohols of the general formula (I).

1- (Dibutylamino) -3,7-dimethyl-6-octene-2,3-diol [Compound (1)]

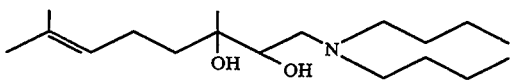

1-(Methylphenylamino)-3,7-dimethyl-6-octene-2,3diol [Compound (2)]

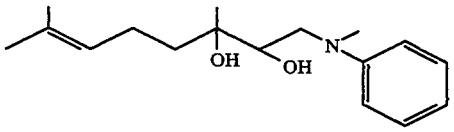

3,7-Dimethyl-1-(1-pyrrolidinyl)-6-octene-2,3-diol [Compound (3)]

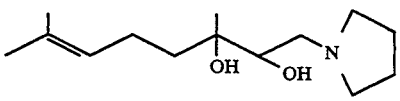

3,7-Dimethyl-1-piperidino-6-octene-2,3-diol [Compound (4)]

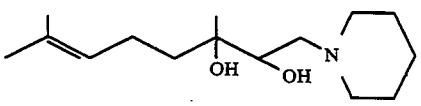

3,7-Dimethyl-1-morpholino-6-octene-2,3-diol [Compound (5)]

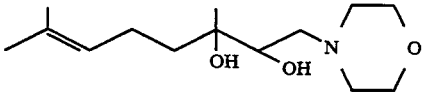

1-[(2-Hydroxyethyl) methylamino]-3,7-dimethyl-6-octene-2,3-diol [Compound (6)]

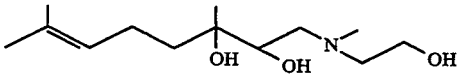

1-Amino-3,7-dimethyl-2,3-octanediol [Compound (7)]

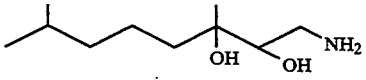

1-(Methylamino)-3,7-dimethyl-2,3-octanediol [Compound (8)]

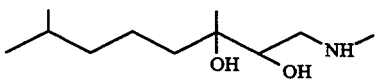

1-(Dibutylamino)-3,7-dimethyl-2,3-octanediol [Compound (9)]

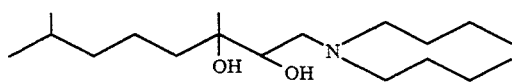

1-[(2-Hydroxyethyl)amino]-3,7-dimethyl-2,3octanediol [Compound (10)]

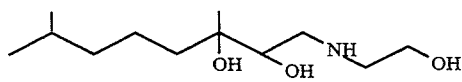

1-Amino-3,7,11-trimethyl-2,3-dodecanediol [Compound (11)]

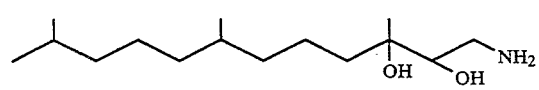

1-(Methylamino)-3,7,11-trimethyl-2,3-dodecanediol [Compound (12)]

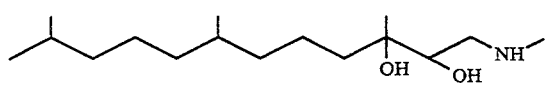

1-(Dibutylamino)-3,7,11-trimethyl-2,3-dodecanedic [Compound (13)]

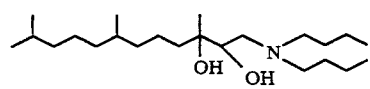

1-[(2-Hydroxyethyl) amino]-3,7,11-trimethyl-2,3dodecanediol [Compound (14)]

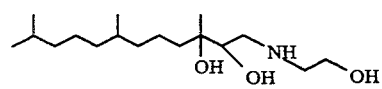

N-Methyl-N-(3,7,11-trimethyl-2,3-dihydroxydodecyl)-nicotinamide [Compound (15)]

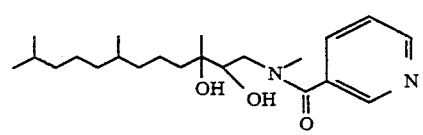

1-(Dimethylamino)-3,7,11-trimethyl-2,3-dodecanediol [Compound (16)]

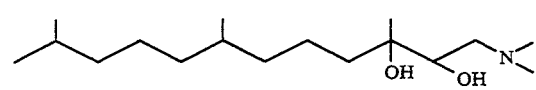

3,7,11-Trimethyl-1-morpholino-2,3-dodecanediol [Compound (17)]

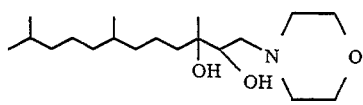

3,7,11-Trimethyl-1-[4-[(2,3,4-trimethoxyphenyl)methyl]piperazin-1-yl]-2,3-dodecanediol [Compound (18)]

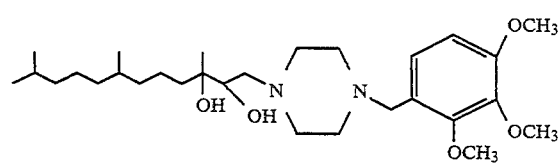

1-[(4-Hydroxyphenyl)amino]-3,7,11-trimethyl-2,3-dodecanediol [Compound (19)]

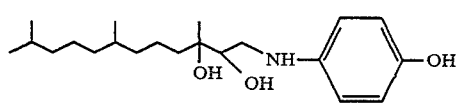

1-[(4-Pyridyl)amino]-3,7,11-trimethyl-2,3-dodecanediol [Compound (20)]

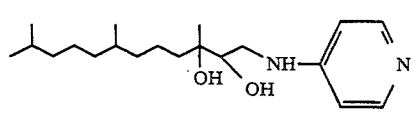

1-(1H-Imidazol-1-yl)-3,7,11-trimethyl-2,3-dodecanediol [Compound (21)]

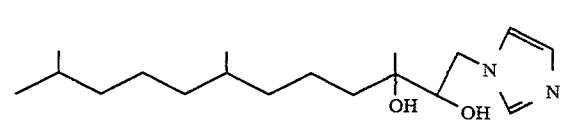

1-(3-Morpholino-1-propyl)amino-3,7,11-trimethyl-2,3-dodecanediol [Compound (22)]

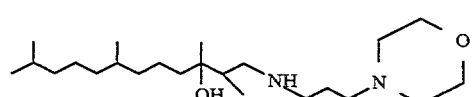

1-(5-Quinolyl)amino-3,7,11-trimethyl-2,3-dodecanediol [Compound (23)]

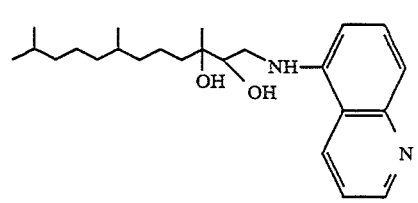

3,7,11-Trimethyl-1-[4-(diphenylmethyl)piperazin-1-yl]2,3-dodecanediol [Compound (24)]

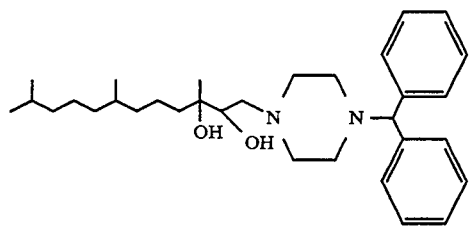

1-(1,3-Dihydro-2-oxo-2H-benzimidazol-1-yl)-3,7,11-trimethyl-2,3-dodecanediol [Compound (25)]

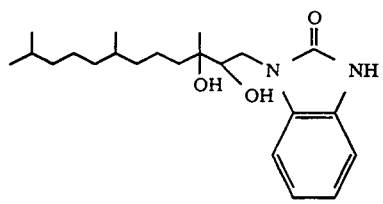

1-(Tetrahydro-2H-1,4-thiazin-4-yl)-3,7,11-trimethyl2,3-dodecanediol [Compound (26)]

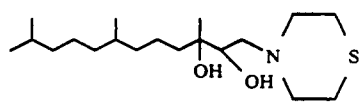

1-(Methylamino)-3,7,11-trimethyl-3,7-dodecanediol [Compound (27)]

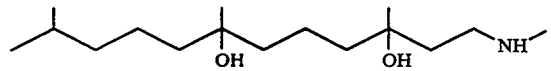

1-(Methylamino)-3,7,11-trimethyl-2-dodecanol [Compound (28)]

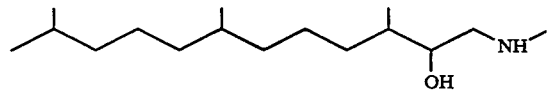

1-(Methylbenzylamino)-3,7,11-trimethyl-3,7-dodecanediol [Compound (29)]

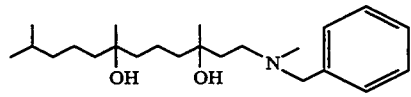

1-Amino-3,7,11,15-tetramethyl-2,3-hexadecanediol [Compound (30)]

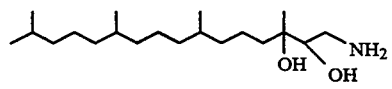

1-(Methylamino)-3,7,11,15-tetramethyl-2,3-hexadecanediol [Compound (31)]

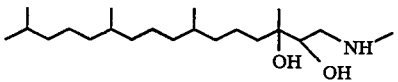

1-(Dimethylamino)-3,7,11,15-tetramethyl-2,3-hexadecanediol [Compound (32)]

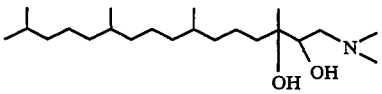

1-(Diethylamino)-3,7,11,15-tetramethyl-2,3-hexadecanediol [Compound (33)]

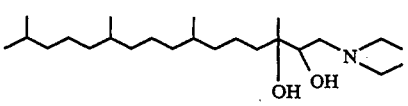

1-(Dibutylamino)-3,7,11,15-tetramethyl-2,3-hexadecanediol [Compound (34)]

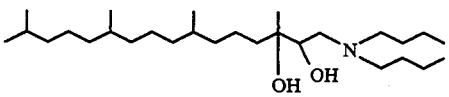

1-[(2-Hydroxyethyl)methylamino]-3,7,11,15-tetramethyl-2,3-hexadecanediol [Compound (35)]

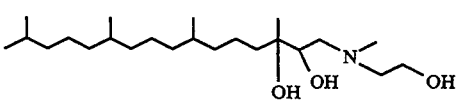

1-[(2-Nicotinoyloxyethyl)methylamino]-3,7,11,15-tetramethyl-2,3-hexadecanediol [Compound (36)]

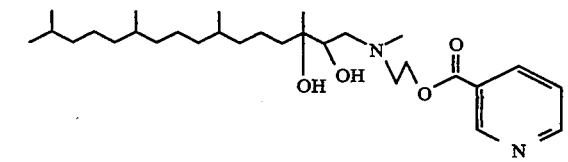

1-(Methylbenzylamino)-3,7,11-trimethyl-3,7,11-dodecanetriol [Compound (37)]

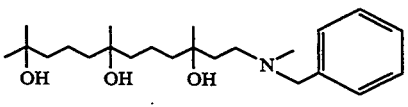

1-(1-Pyrrolidinyl)-3,7,11-trimethyl-2,3-dodecanediol [Compound (38)]

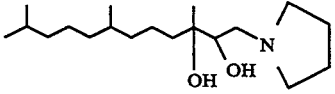

1-Piperidino-3,7,11-trimethyl-2,3-dodecanediol [Compound (39)]

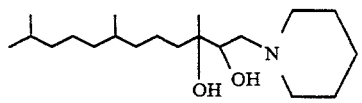

1-[(1-Benzylpiperidin-4-yl)amino]-3,7,11-trimethyl2,3-dodecanediol [Compound (40)]

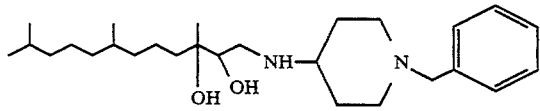

1-[(3-Pyridyl)methylamino]-3,7,11-trimethyl2,3-dodecanediol [Compound (41)]

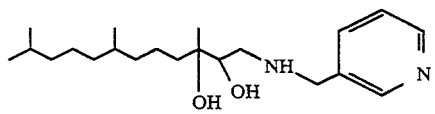

1-[4-(2-Methoxyphenyl)-1-piperazinyl]-3,7,11-trimethyl-2,3-dodecanediol [Compound (42)]

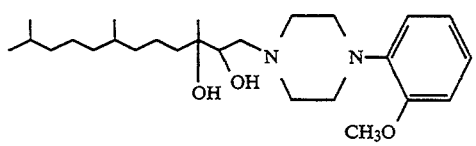

1-Amino-3,7-dimethyl-6-octene-2,3-diol [Compound (43)]

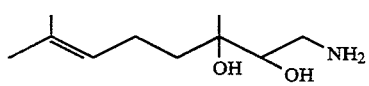

1-(Methylamino)-3,7-dimethyl-6-octene-2,3-diol [Compound (44)]

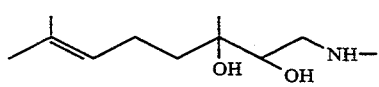

1-(Dimethylamino)-3,7-dimethyl-6-octene-2,3-diol [Compound (45)]

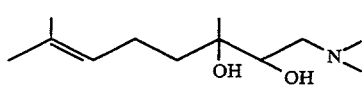

1-(Ethylamino)-3,7-dimethyl-6-octene-2,3-diol [Compound (46)]

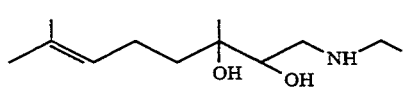

1-(Propylamino)-3,7-dimethyl-6-octene-2,3-diol [Compound (47)]

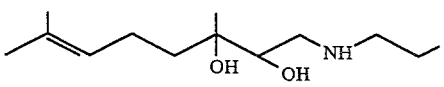

1-(Diethylamino)-3,7-dimethyl-6-octene-2,3-diol [Compound (48)]

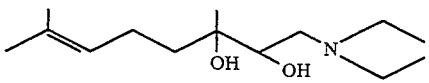

1-(Butylamino)-3,7-dimethyl-6-octene-2,3-diol [Compound (49)]

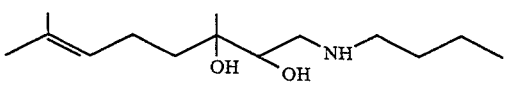

2-Amino-3,7-dimethyl-6-octene-1,3-diol [Compound (50)]

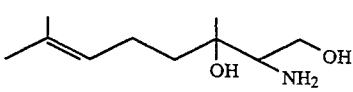

2-(Dimethylamino)-3,7-dimethyl-6-octene-1,3-diol [Compound (51)]

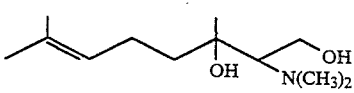

2-(Propylamino)-3,7-dimethyl-6-octene-1,3-diol [Compound (52)]

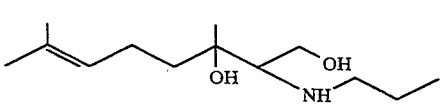

2-(Dibutylamino)-3,7-dimethyl-6-octene-1,3-diol [Compound (53)]

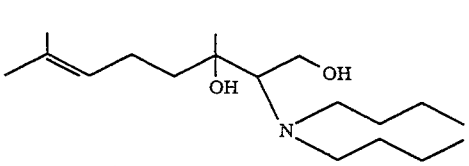

3,7-Dimethyl-2-(1-pyrrolidinyl)-6-octene-1,3-diol [Compound (54)]

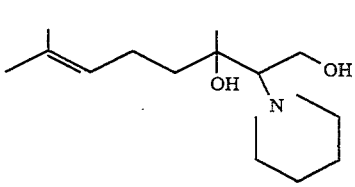

3,7-Dimethyl-2-piperidino-6-octene-1,3-diol [Compound (55)]

3,7-Dimethyl-2-morpholino-6-octone-1,3-diol [Compound (56)]

2-[(2-Hydroxyethyl)methylamino]-3,7-dimethyl-6-octene-1,3-diol [Compound (57)]

2-Amine-3,7-dimethyl-1,3-octanediol [Compound (58)]

2-(Dibutylamino)-3,7-dimethyl-1,3-octanediol [Compound (59)]

2-[(2-Hydroxyethyl)methylamino]-3,7-dimethyl-1,3-octanediol [Compound (60)]

2-Amino-3,7,11-trimethyl-3-dodecanol [Compound (61)]

2-(Methylamino)-3,7,11-trimethyl-1,3-dodecanediol [Compound (62)]

2-[(1-Benzylpiperidin-4-yl) amino]-3,7,11-trimethyl-1,3-dodecanediol [Compound (63)]

2-(1H-Imidazol-1-yl)-3,7,11-trimethyl-1,3-dodecanediol [Compound (64)]

3,7,11-Trimethyl-2-[4-[(2,3,4-trimethoxyphenyl)methyl]piperazin-1-yl]-1,3-dodecanediol [Compound (65)]

N-Methyl-N-(1,3-dihydroxy-3,7,11-trimethyldodecan-2-yl)nicotinamide [Compound (66)]

2-[(2-Hydroxyethyl)amino]-3,7,11-trimethyl-1,3-dodecanediol [Compound (67)]

2-(Tetrahydro-2H-1,4-thiazin-4-yl)-3,7,11-trimethyl-1,3-dodecanediol [Compound (68)]

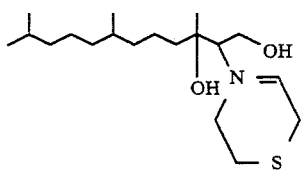

2-(3-Morpholinopropyl) amino-3,7,11-trimethyl-1,3-dodecanediol [Compound (69)]

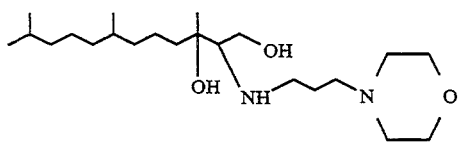

2-(Methylamino)-3,7,11-trimethyl-3,7-dodecanediol [Compound (70)]

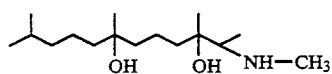

2-(Benzylmethylamino)-3,7,11-trimethyl-3,7-dodecanediol [Compound (71)]

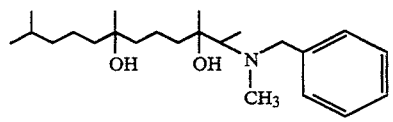

2-(Dimethylamino)-3,7,11,15-tetramethyl-1,3-hexadecanediol [Compound (72)]

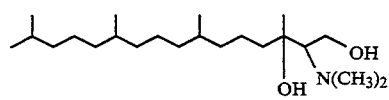

2-[(2-Hydroxyethylmethylamino]-3,7,11,15-tetramethyl-1,3-hexadecanediol [Compound (73)]

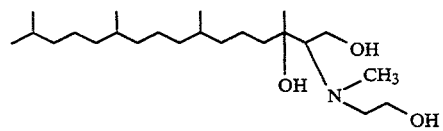

2-[(2-Nicotinoyloxyethyl)methylamino]-3,7,11,15-tetramethyl-1,3-hexadecanediol [Compound (74)]

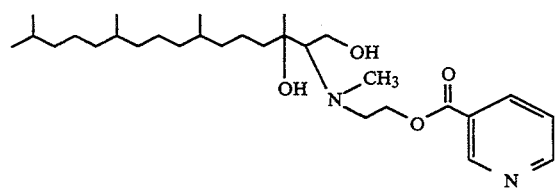

The pharmacologically acceptable esters off the terpene amino alcohol off general formula (I) include, among others, esters with lower fatty acids such as acetic acid, propionic acid, butyric acid, etc.; esters with higher fatty acids such as palmitic acid, linolic acid, oleic acid, stearic acid, etc.; and esters with nicotinic acid, benzoic acid, phosphoric acid, monomannosylphosphoric acid, etc. The pharmacologically acceptable salts include, among others, salts with mineral acids such as hydrochloric acid, sulfuric acid, etc.; salts with organic sulfonic acids such as methanesulfonic acid, p-toluenesulfonic acid, etc.; and salts with organic carboxylic acids such as acetic acid, propionic acid, succinic acid, lactic acid, tartaric acid, malic acid, citric acid and so on.

Terpene amino alcohols of general formula (I) are divided into the following two types.

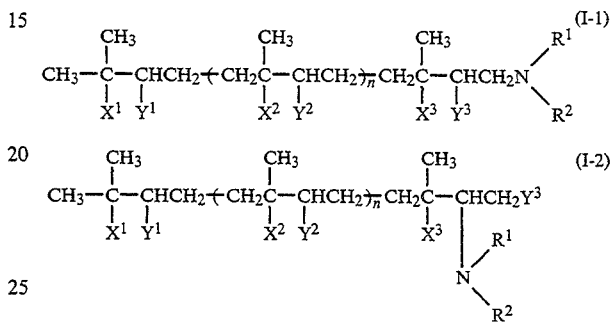

In the above formulas $X^1$, $Y^1$, $X^2$, $Y^2$, $X^3$, $Y^3$, $R^1$, $R^2$ and $\underline{n}$ are as defined hereinbefore.

The terpene amino alcohol of general formula (I-1) can be produced by the following methods (i) and (ii), for instance.

Method (i)

The compound of general formula (I-1) wherein $Y^3$ is a hydroxyl group

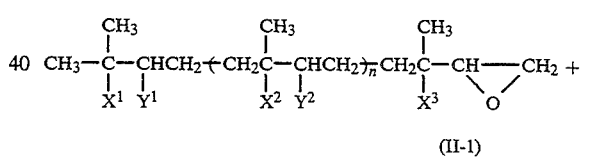

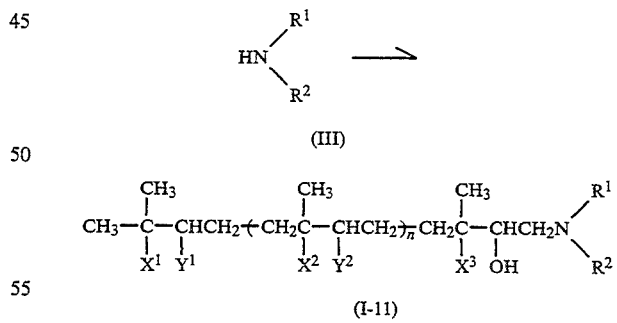

In the above formulas, $X^1$, $Y^1$, $X^2$, $Y^2$, $X^3$, $R^1$, $R^2$ and $\underline{n}$ are as defined hereinbefore.

Thus, an epoxyterpene of general formula (II-1) is reacted with an organic amino compound of general formula (III) under heating to give a terpene amino alcohol of general formula (I-11). Alternatively, an organic amino-compound of general formula (III) is first reacted with an alkali metal such as lithium, sodium, potassium, etc., an organolithium compound such as methyllithium, n-butyllithium, phenyllithium, etc. or a Grignard reagent such as methylmagnesium bromide, methylmagnesium chloride, ethylmagnesium bromide, ethylmagnesium chloride, etc. to give the corresponding metal salt of the organic amino compound, which is then reacted with said epoxyterpene of general formula (II-1) to give a terpene amino alcohol of general formula (I-11). The reaction between the epoxyterpene of general formula (II-1) and the organic amino compound of general formula (III) is generally carried out in the presence or absence of an inert solvent such as methanol, ethanol, dioxane, etc. at a temperature of about 80° to 200° C. The organic amino compound is used in a proportion of about 1 to 5 moles per mole of the epoxyterpene. When the boiling point of the organic amino compound is lower than the reaction temperature, the reaction is advantageously carried out under elevated pressure. The organic amino compound can be used in aqueous condition, e.g. in the presence of aqueous ammonia, an aqueous solution of methylamine or the like. The reaction time varies with the reaction temperature used but is generally in the range of about 1 to 24 hours. The reaction for conversion of the organic amino compound of general formula (III) to the metal salt thereof is carried out in the known manner using an alkali metal, an organolithium compound or a Grignard reagent on an equimolar basis. The reaction between the resulting metal salt of the organic amino compound and the epoxyterpene of general formula (II-1) can be carried out in the same manner as the reaction between said epoxyterpene and the organic amino compound of general formula (III) except that the reaction temperature used may range from about 0° C. to about 100° C.

The starting material epoxyterpene of general formula (II-1) can be prepared, for example by the following procedures (a) and (b).

Procedure (a) The compound of general formula (II-1) wherein $X^3$ is a hydroxyl group

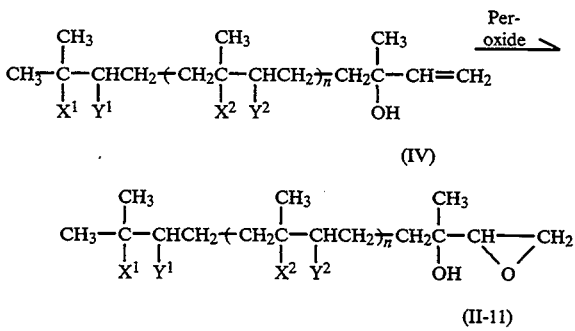

In the above formulas, $X^1$, $Y^1$, $X^2$, $Y^2$ and $\underline{n}$ are as defined hereinbefore.

The epoxyterpene of general formula (II-11) can be prepared by reacting an allyl alcohol of general formula (IV) with a peroxide such as t-butyl hydroperoxide, cumene hydroperoxide or the like in the presence of a vanadium or molybdenum catalyst in the conventional manner [J. Am. Chem. Soc. 95, 6136 (1973)].

Procedure (b) The compound of general formula (II-1) wherein $X^3$ is a hydrogen atom

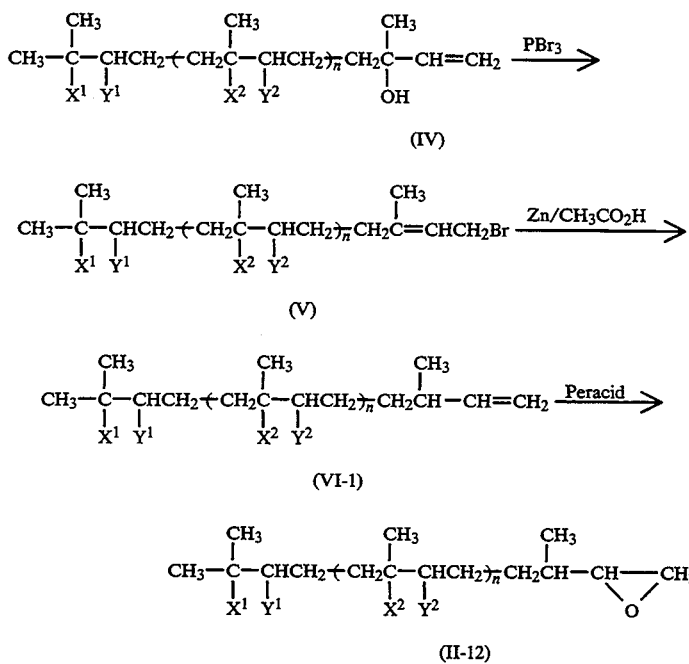

In the above formulas, $X^1$, $Y^1$, $X^2$, $Y^2$ and $\underline{n}$ are as defined hereinbefore.

The epoxyterpene of general formula (II-12) can be prepared by the steps comprising treating an allyl alcohol of general formula (IV) with phosphorus tribromide, reducing the resulting bromide of general formula (V) with zinc-acetic acid to give a terpene of general formula (VI-1), and finally reacting the terpene with a peracid such as perbenzoic acid, meta-chloroperbenzoic acid, peracetic acid, etc.

Method (ii)

The compound of general formula (I-1) wherein $X^2$ and $X^3$ each is a hydroxyl group; $Y^2$ and $Y^3$ each is a hydrogen atom; and $\underline{n}$ is equal to 1

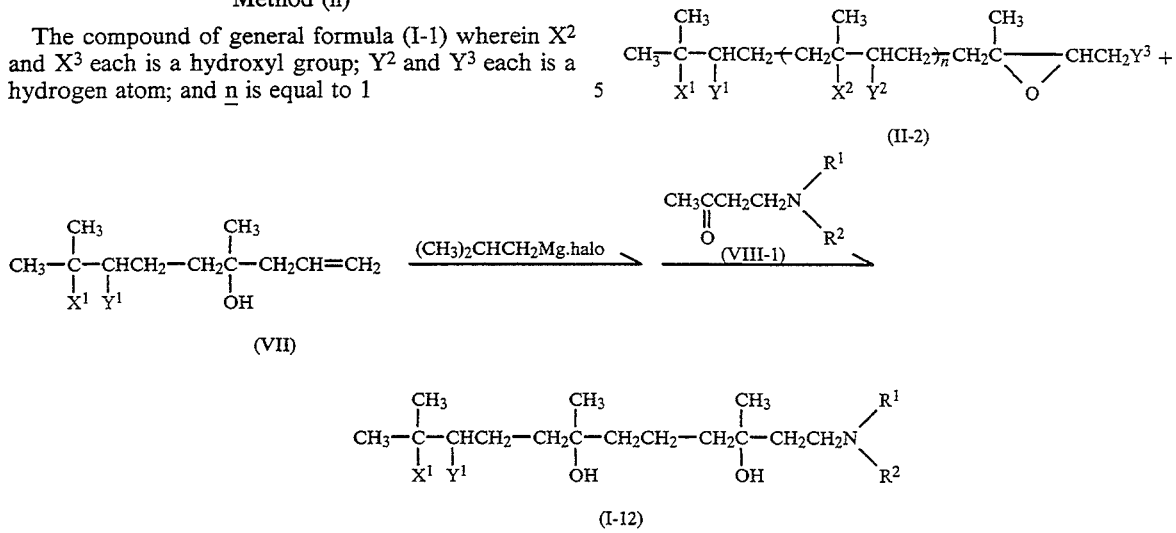

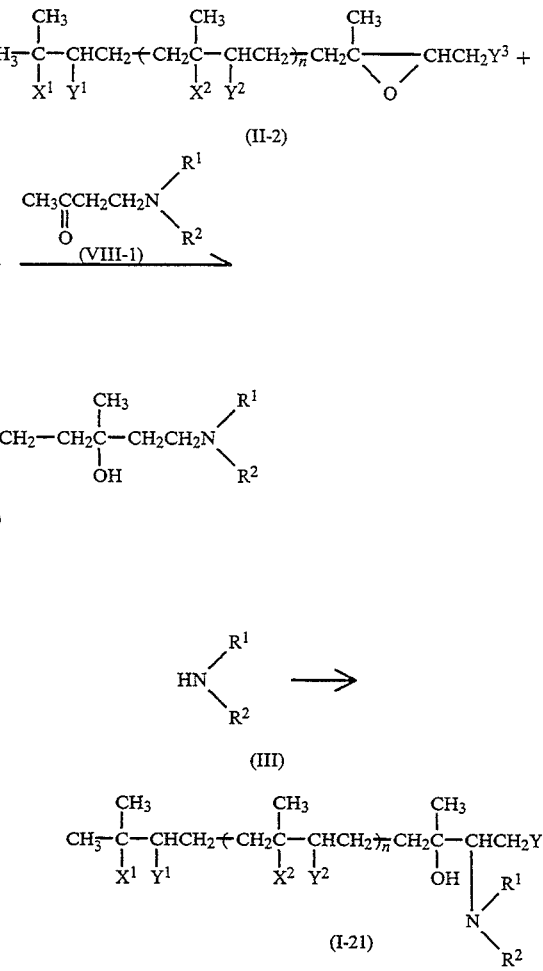

In the above formulas, $X^1$, $Y^1$, $R^1$ and $R^2$ are as defined hereinbefore; $\underline{halo}$ means a halogen atom.

Thus, the terpene amino alcohol of general formula (1-12) can be prepared by the steps comprising reacting an alcohol of general formula (VII) with an isobutylmagnesium halide such as isobutylmagnesium chloride, isobutylmagnesium bromide, etc. in the presence of titanocene dichloride to give a Grignard reagent and reacting an aminoketone of general formula (VIII-1) with said Grignard reagent. The reaction giving the Grignard reagent is preferably carried out in a solvent such as tetrahydrofuran etc. The proportion of titanocene dichloride is about 1 to 10 mole percent relative to the starting material alcohol of general formula (VII) and, preferably in the range of about 3 to 7 mole percent on the same basis. The proportion of said isobutylmagnesium halide depends on the number of hydroxyl groups in the alcohol of general formula (VII). Thus, it is about 2 molar equivalents for the alcohol having one hydroxyl group, about 3 molar equivalents for the alcohol having two hydroxyl groups, and about 4 molar equivalents for the alcohol having 3 hydroxyl groups. This reaction is generally carried out by the steps comprising adding a solution of the isobutylmagnesium halide in tetrahydrofuran dropwise to a solution of the alcohol of general formula (VII) in tetrahydrofuran at a temperature of about $-10°$ C. to 50° C. and, then, adding titanocene dichloride thereto at a temperature of about 15° to 35° C., followed by stirring the resulting mixture for about 3 to 10 hours. The reaction between the Grignard reagent thus prepared and the aminoketone of general formula (VIII-1) is generally carried out by the steps comprising adding said aminoketone dropwise to the Grignard reagent solution prepared as above and stirring the mixture at a temperature of about 0° to 50° C. for about 1 to 10 hours. The preferable amount of the aminoketone is about 0.7 to 2 molar equivalents relative to the alcohol of general formula (VII) used in the preparation of the Grignard reagent.

The terpene amino alcohol of general formula (I-2) can be produced, for example by the following methods (iii) and (iv).

Method (iii)

The compound of general formula ( i-2) wherein $X^3$ is a hydroxyl group

In the above formulas, $X^1$, $Y^1$, $X^2$, $Y^2$, $Y^3$, $R^1$, $R^2$ and $\underline{n}$ are as defined hereinbefore.

In this method, an epoxyterpene of general formula (II-2) is reacted with an organic amino compound of general formula (III) in the same manner as the reaction between the epoxyterpene of general formula (II-1) and the organic amino compound of general formula (III) according to the above-mentioned Method (i).

The starting material epoxyterpene of general formula (II-2) can be prepared, for example by the following procedure.

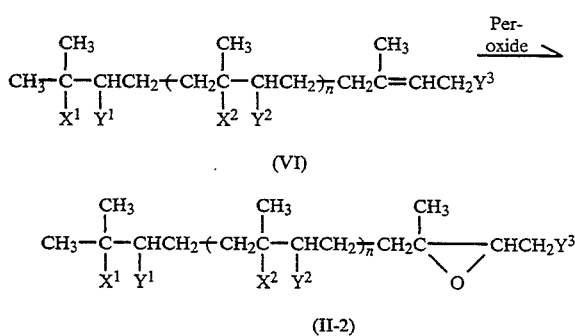

In the above formulas, $X^1$, $Y^1$, $X^2$, $Y^2$, $Y^3$ and $\underline{n}$ are as defined hereinbefore.

The epoxyterpene of general formula (II-2) can be prepared, for example by reacting an allyl alcohol of general formula (VI) with a peroxide such as t-butyl hydroperoxide, cumene hydroperoxide, etc. in the presence of a vanadium or molybdenum catalyst in the conventional manner [J. Am. Chem. Soc. 95, 6136 (1973)].

Method (iv)

The compound of general formula (I-2) wherein $X^2$ and $X^3$ each is a hydroxyl group; $Y^2$ is a hydrogen atom; and $\underline{n}$ is equal to 1

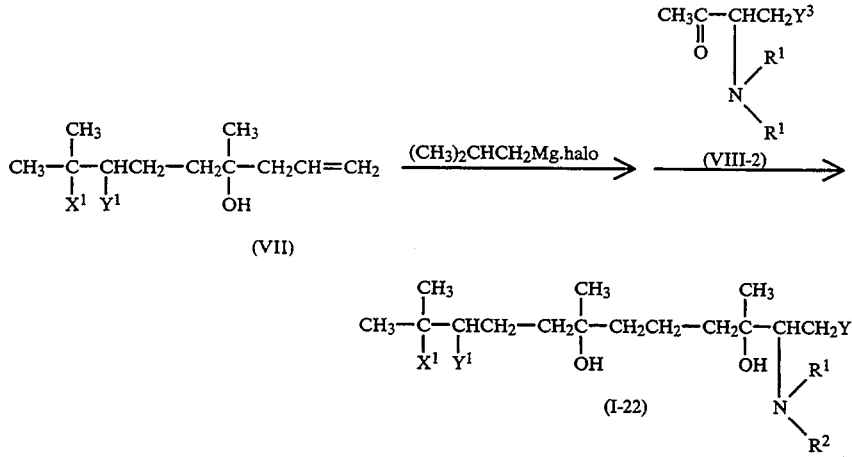

In the above formulas, $X^1, Y^1, Y^3, R^1, R^2$ and $\underline{halo}$ are as defined hereinbefore.

Like the previous method (ii), the terpene amino alcohol of general formula (I-22) can be prepared by the steps comprising reacting an alcohol of general formula (VII) with an isobutylmagnesium halide in the presence of titanocene dichloride and reacting an aminoketone of general formula (VIII) with the resulting Grignard reagent.

The resulting reaction mixture containing the terpene amino alcohol of general formula (I) is then directly distilled or the residue after removal of a low boiling fraction from the reaction mixture by distillation is subjected to distillation under reduced pressure or column chromatography. Alternatively, said reaction mixture is poured into water, a saturated aqueous solution of ammonium chloride or the like and extracted with diethyl ether, dichloroethane or the like. The extract is washed with water, an aqueous solution of sodium hydrogen carbonate or the like and dried over anhydrous magnesium sulfate etc., followed by removal of the solvent. The residue is then subjected to distillation under reduced pressure or column chromatography. By any of the above methods, the terpene amino alcohol (I) can be isolated.

The following test examples illustrate the pharmacological characteristics of the terpene amino alcohols provided by the present invention.

TEST EXAMPLE 1

Antiallergic Action

Test method

Male guinea pigs of Hartley strain (body weight: about 250 g) were intraperitoneally or intramuscularly dosed with egg albumin (dose 100 mg/kg) and the same procedure was repeated after 3 days. After 3 to 4 weeks, the guinea pigs were bled to death and the sensitized bronchial muscle was excised and cut into 1.5 mm thick rings. Three rings were joined to prepare a specimen. The specimen was suspended in a tissue bath and a load of 1 g was applied. The bath temperature was maintained at 37° C. and a mixture gas of 95% $O_2$ and 5% $CO_2$ was constantly bubbled into the bath. After stabilization of the specimen (after about 1 hour), histamine hydrochloride was added to the bath at a final concentration of $10^{-5}$M. The contraction curve was recorded. After the contraction had been stabilized, the specimen was washed with 3 portions of Ringer's solution at 10-minute intervals to stabilize the contraction (about 1 hour was required). Then, the test compound was added to the tissue bath and, after an interval of 10 minutes, 5 mg/ml of egg albumin was added. The contraction amplitude of the specimen was measured and the percent inhibition was calculated according to the following formula.

$$\text{Inhibition (\%)} = \left(1 - \frac{A'/H'}{A/H}\right) \times 100$$

A: Contraction amplitude of control group when egg albumin is added

A': Contraction amplitude of dosage group when egg albumin is added

H: Contraction amplitude of control group when histamine hydrochloride is added

H': Contraction amplitude of dosage group when histamine hydrochloride is added

Test results

The concentrations of test compounds and the inhibition percents are shown in Table 1.

TABLE 1

| Test compound | Inhibition (%) | | | | |
|---|---|---|---|---|---|
| | $10^{-4}$M | $10^{-5}$M | $10^{-6}$M | $10^{-7}$M | $10^{-8}$M |
| Tranilast | 32.1 | 54.8 | 21.0 | 0 | 0 |
| Disodium cromoglicate | 32.1 | 21.0 | 7.8 | 0 | 0 |
| 1 | 43.6 | — | — | — | — |
| 2 | 58.7 | 30.1 | 19.9 | — | — |
| 3 | — | 36.3 | 60 | 34.2 | 30.8 |
| 4 | — | 42.0 | 2.6 | — | — |
| 5 | — | 28.9 | 71.46 | 23 | — |
| 6 | — | 48.2 | 28.6 | — | — |
| 7 | — | 54.3 | 48.1 | 58.7 | — |
| 8 | 52.6 | 37.8 | — | — | — |
| 9 | — | 27.9 | 67.2 | 56 | 16 |
| 10 | 81.2 | 23.8 | — | — | — |

TABLE 1-continued

| Test compound | Inhibition (%) | | | | |
|---|---|---|---|---|---|
| | $10^{-4}M$ | $10^{-5}M$ | $10^{-6}M$ | $10^{-7}M$ | $10^{-8}M$ |
| 11 | — | 40.7 | 32.5 | — | — |
| 12 | 48.3 | 35.4 | — | — | — |
| 13 | 40.2 | — | — | — | — |
| 14 | — | 48.7 | 51.4 | — | — |
| 15 | 72.53 | 67.03 | 93.01 | — | — |
| 16 | — | 48 | 35 | 15 | — |
| 17 | — | 45 | 68 | 29 | — |
| 18 | — | 62 | 79 | 45 | — |
| 19 | — | 43 | 54 | 33 | — |
| 20 | — | — | 71 | 40 | 15 |
| 21 | — | — | — | 66.9 | — |
| 22 | — | — | — | 46.9 | — |
| 23 | — | — | 76 | 55 | 27 |
| 24 | — | — | 75 | 60 | 25 |
| 25 | — | — | 69 | 47 | 19 |
| 26 | — | 50 | 39 | 18 | — |
| 27 | — | — | — | 15.6 | — |
| 28 | — | 66 | 49 | 35 | — |
| 29 | — | — | — | 42.3 | — |
| 30 | — | 16.7 | 9.0 | — | — |
| 31 | — | 10.9 | — | — | — |
| 32 | — | 40.0 | 61.1 | 25.0 | 10.0 |
| 33 | — | 47.9 | 32.6 | — | — |
| 34 | — | 65.2 | 33.0 | 3.0 | — |
| 35 | — | 27.1 | 85.5 | 35.0 | 22.0 |
| 36 | — | 45 | 20 | 8 | — |
| 37 | — | — | — | 16 | — |
| 38 | — | — | — | 36.7 | — |
| 39 | — | — | — | 29.1 | — |
| 40 | — | — | — | 34.8 | — |
| 41 | — | — | — | 46 | — |
| 42 | — | — | 58 | 35 | — |
| 43 | — | — | 65 | — | — |
| 44 | — | 63 | 54 | — | — |
| 45 | 52 | 41 | 26 | — | — |
| 46 | 38 | 54 | 23 | — | — |
| 47 | — | 52 | 43 | 5.0 | — |
| 48 | — | 47 | 310 | — | — |
| 49 | — | — | 61 | 20.7 | — |
| 50 | — | 55 | 20 | 0 | — |
| 51 | — | 41 | 18 | 0 | — |
| 52 | — | 62 | 31 | 7 | 0 |
| 53 | — | 33 | 59 | 49 | 8 |
| 54 | — | 54 | 63 | 33 | 20 |
| 55 | — | 45 | 17 | 9 | 0 |
| 56 | — | 27 | 44 | 16 | 0 |
| 57 | — | 35 | 17 | — | — |
| 58 | 21 | 0 | 0 | — | — |
| 59 | — | 49 | 51 | 0 | — |
| 60 | — | 35 | 11 | 0 | — |
| 61 | — | 70 | 48 | 24 | — |
| 62 | — | 39 | 35 | 12 | — |
| 63 | — | — | 55 | 45 | 11 |
| 64 | — | — | — | 63 | — |
| 65 | — | 73 | 54 | 37 | — |
| 66 | — | 77 | 72 | 81 | — |
| 67 | — | 46 | 49 | 18 | — |
| 68 | — | 38 | 36 | 22 | — |
| 69 | — | — | 65 | 52 | — |
| 70 | — | 42 | 19 | — | — |
| 71 | — | — | 37 | 46 | — |
| 72 | — | 51 | 60 | 24 | 9 |
| 73 | — | 36 | 58 | 47 | 21 |
| 74 | — | 43 | 16 | 20 | — |

It will be apparent from Table 1 that all the test compounds produce antiallergic effects and that most of the compounds according to the present invention display stronger antiallergic activity as compared with the control drugs tranilast and disodium cromoglicate.

Thus, the terpene amino alcohols have excellent properties as antiallergic agents.

TEST EXAMPLE 2

Effect of improving the memories of amnesia models

1. Test animals

The test was performed using male mice of ddK strain (5-6 weeks of age, 6-8 animals per group) at room temperature (about 23° C.). The mice were allowed to take feeds and water freely.

2. Effects on memorized behaviors (1) Experimental device

The device comprised a dark chamber (a rectangular box 20 cm high, with a floor grid, 12 cm ×15 cm) and a bright chamber (a box with an open top and a floor grid, 15 cm ×15 cm, surrounded by rectangular walls, 15 cm$^W$ ×20 cm$^W$, on four sides). The two chambers were in contact with each other sharing a common surface of 15 cm ×20 cm which is provided with an opening through which the mouse could move freely. A stainless steel wire, which was connected to an electric impulse apparatus (manufactured by Nippon Medical and Chemical Instruments Co., Ltd.), was placed on the floor grid in the dark chamber. The bright chamber was illuminated with a 60 W electric bulb from a height of about 45 cm above the floor grid.

(2) Acquisition trials

Each mouse was placed on the floor grid in the bright chamber. Immediately after the mouse (four limbs) entered the dark chamber, it was loaded with an electroshock of DC 50 V through the floor grid for about three seconds. Immediately after electroshock loading, the mouse was taken out from the dark chamber.

(3) Test trials

Twenty-four hours after acquisition trials, each mouse was placed on the floor grid in the bright chamber again and the time which elapsed until the mouse (four limbs) entered the dark chamber (latency) was measured up to 600 seconds.

3. Preparation of amnesia-induced animals (1) $CO_2$-induced amnesia

Immediately after the acquisition trials, each mouse was left in a container filled with carbon dioxide for a period of 8 seconds to induce amnesia.

(2) Scopolamine-induced amnesia

Scopolamine, 3 mg, was administered intraperitoneally to mice to induce amnesia 20 minutes before initiation of acquisition trials.

4. Administration of test compounds

A 5% aqueous suspension of each test compound in gum arabic solution was administered orally to mice immediately after carbon dioxide loading or to mice immediately after completion of the acquisition trials following scopolamine administration.

5. Results

The effects of test compounds on $CO_2$-induced amnesia are shown in Table 2. The effects of test compounds on scopolamine-induced amnesia are shown in Table 3.

TABLE 2

| Test compound | Dose (mg/kg) | Latency (sec.) Mean ± S.E. |
|---|---|---|
| (Normal mice) | — | 382.4 ± 83.6 |
| ($CO_2$-treated mice) | — | 138.2 ± 43.6 |
| Compound (35) | 100 | 258.4 ± 94.5 |
| (Normal mice) | — | 375.7 ± 74.9* |
| ($CO_2$-treated mice) | — | 139.4 ± 27.5 |
| Compound (36) | 100 | 336.6 ± 77.8* |
| ($CO_2$-treated mice) | — | 37.6 ± 19.6 |

TABLE 2-continued

| Test compound | Dose (mg/kg) | Latency (sec.) Mean ± S.E. |
|---|---|---|
| Compound (36) | 100 | 216.0 ± 69.0 |
| Compound (15) | 100 | 163.9 ± 49.1 |
| (Normal mice) | — | 394.2 ± 84.0* |
| (CO$_2$-treated mice) | — | 106.5 ± 24.9 |
| Calcium hopantenate | 100 | 115.5 ± 40.6 |
| Pramiracetam | 100 | 175.8 ± 42.9 |

*$P < 0.05$

Whereas calcium hopantenate and pramiracetam failed to show a significant memory activating action, Compound (36) very significantly improved the shortening of latency induced by carbon dioxide, displaying an excellent memory activating action. Compound (15) and Compound (35) also showed a tendency to activate memory.

TABLE 3

| Test compound | Dose (mg/kg) | Latency (sec.) Mean ± S.E. |
|---|---|---|
| (Normal mice) | — | 382.4 ± 83.6 |
| (Scopolamine-treated mice) | — | 169.0 ± 53.0 |
| Compound (35) | 100 | 320.2 ± 66.2 |
| (Normal mice) | — | 375.7 ± 74.9* |
| (Scopolamine-treated mice) | — | 166.7 ± 36.7 |
| Compound (36) | 100 | 336.2 ± 55.4* |
| (Scopolamine-treated mice | — | 54.6 ± 14.5 |
| Compound (36) | 100 | 78.5 ± 26.9 |
| Compound (15) | 100 | 65.2 ± 20.2 |
| (Normal mice) | — | 394.2 ± 84.0** |
| (Scopolamine-treated mice) | — | 83.5 ± 21.5 |
| Calcium hopantenate | 100 | 80.5 ± 17.2 |
| Pramiracetam | 100 | 98.1 ± 24.9 |

*$P < 0.05$,
**$P < 0.01$

Compared with calcium hopantenate and pramiracetam, Compound (35) and Compound (36) each significantly improved the shortening of latency induced by scopolamine.

TEST EXAMPLE 3

KCN anoxia test

Male mice of ddK strain (5-6 weeks of age, 8 to 10 animals per group) were intraperitoneally dosed with predetermined amounts of test compounds and after an interval of 30 minutes, 2.65 mg/kg of potassium cyanide was intravenously administered. Mice which showed no respiratory arrest even after a lapse of 180 seconds were counted as survival cases and the survival rate was calculated. The results are shown in Table 4.

TABLE 4

| Test compound | Dose (mg/kg) | Number of survivals/ Number of mice used | Survival rate (%) |
|---|---|---|---|
| Control | — | 0/8 | 0 |
| Compound (35) | 100 | 8/9 | 88.9** |
| Compound (15) | 100 | 7/9 | 77.8* |
| Dihydroergotoxine mesilate | 3 | 1/10 | 10.0 |

*$P < 0.05$,
**$P < 0.01$

The death due to potassium cyanide is caused by the fact that the compound inhibits the enzyme involved in the electron transfer system of mitochondria in cells and the brain cells are liable to be affected by potassium cyanide. It has been reported that dihydroergotoxine mesilate, known as a drug for improving cerebral metabolism, promotes cerebral glucose uptake and oxidation of succinic acid in mitochondria and increases the cerebral blood flow, and while dihydroergotoxine mesilate displays an anti-anoxic effect because of these actions, this effect is not sufficiently remarkable. It is apparent from Table 4 that Compound (35) and Compound (15) show a significantly high anti-anoxic action.

Thus, the terpene amino alcohols according to the present invention have excellent characteristics as agents for improving cerebral function.

Toxicity studies also made it clear that the terpene amino alcohols according to the present invention are of low toxicity. By way of illustration, the acute toxicity, the LD$_{50}$ value of Compound (32) in mice (male mice of ddK strain, body weights 20-23 g, 10 animals per group, oral) was 3,875 mg/kg and the LD$_{50}$ values of Compounds (1) to (31) and (33) to (74) were respectively more than 3,500 mg/kg.

As demonstrated by the results of the above pharmacological studies, the terpene amino alcohols according to the present invention can be used as medicaments for the prevention and treatment of various symptoms and signs attributed to allergic reactions such as bronchial asthma, allergic rhinitis, urticaria and so on. Furthermore, the terpene amino alcohols according to the present invention can be used as agents for improving cerebral function, i.e. medicaments for the prevention and/or treatment of various impediments in cerebral function induced by derangement in the regulation of metabolism in the brain. For example, these terpene amino alcohols show excellent prophylactic and/or therapeutic efficacy of dementia attributed to head trauma, a surgical operation on the brain, cerebrovascular disorder, etc., dementia attributed to endocrine and metabolic disorders such as hyperthyroidism, hypothyroidism, accessory thyroidal disease, Wilson disease, hepatopathy, hyperlipemia, hypoglycemia, hypercalcemia, hypocalcemia, Cushing syndrome, hypopituitarism, uremia, etc.; dementia attributed to hypoxic diseases such as cardio-pulmonary disorders, anemia, etc.; dementia attributed to infectious diseases such as brain abscess, bacillary meningitis, tuberculous meningitis, syphilis, cerebral helminthiasis; and Alzheimer-type senile dementia and other dementia attributed to extensive parenchymal lesions of the central nervous system such as Pick disease, Huntington disease, Parkinson disease and so on.

For use as a prophylactic and/or therapeutic agent for the above-mentioned various symptoms attributed to allergic reactions or for the above-mentioned various impediments in cerebral function, the terpene amino alcohol according to the present invention is used at a dose that is dependent upon the object and method of administration, the condition, body weight, age and sex of the patient to be treated, the judgement of the doctor in charge, and other factors. In the case of humans, the daily dose may range generally from about 25 to 300 mg/kg/day, preferably from about 30 to 200 mg/kg/day, and more desirably from about 50 to 100 mg/kg/day, and may be administered at a time or in a few divided portions a day. Any dosage form suited for administration of said compound can be used.

The route of administration may be whichever of oral and non-oral routes. For non-oral administration, not only intravascular routes such as intravenous and intraarterial routes but also intramuscular, intraperitoneal, intraspinal, intrarectal and other routes can be employed.

For administering the terpene amino alcohol, it may be formulated with an appropriate pharmaceutically acceptable diluent or vehicle to provide dosage forms suited for the above-mentioned respective routes of administration, such as tablets, granules, powders, coated tablets, hard capsules, elastic capsules, syrups and so on. The compound may also be formulated into parenteral dosage forms suitable for injection or intravenous drip infusion such as suspensions, solutions, oily or aqueous emulsions and so on. These dosage forms can be manufactured by the established pharmaceutical procedures. Thus, the present invention encompasses pharmaceutical compositions and products containing at least one member of the terpene amino alcohols that is a medicinally useful compound.

When such a composition or product is an oral preparation, it is desirably provided in forms suitable for absorption through the gastrointestinal tract. Tablets and capsules for oral administration, which are unit dosage forms, may contain conventional auxiliaries which are generally used in the pharmaceutical field, e.g. binders such as syrup, gum arabic, gelatin, sorbitol, gum tragacanth, polyvinylpyrrolidone, etc., excipients such as lactose, sucrose, corn starch, calcium phosphate, sorbitol, glycine, etc., lubricants such as magnesium stearate, talc, polyethylene glycol, silica, etc., disintegrators such as potato starch etc., pharmaceutically acceptable wetting agents such as sodium laurylsulfate, and so on. Tablets may be coated in the well-known manner. Liquid preparations for oral administration include aqueous or oily suspensions, solutions, syrups, elixirs, and so on, or may be lyophilisates for extemporaneous reconstitution with water or a suitable other vehicle. Such liquid preparations may contain those auxiliaries which are commonly used in the pharmaceutical field, e.g. suspending agents such as sorbitol syrup, methylcellulose, glucose/sucrose syrup, gelatin, hydroxyethylcellulose, carboxymethylcellulose, aluminum stearate gel, hydrogenated edible fat, etc., emulsifiers such as lecithin, sorbitan monooleate, gum arabic, etc., non-aqueous vehicles such as almond oil, fractionated coconut oil, oily esters, propylene glycol, ethyl alcohol, etc., and preservatives such as methyl p-hydroxybenzoate, propyl p-hydroxybenzoate, sorbic acid, and so on.

In preparing parenteral products, the terpene amino alcohol may be formulated with a pH-adjusting agent, buffer, stabilizer, preservative and/or solubilizer, for instance, in the routine manner.

The pharmaceutical compositions according to the present invention may contain, in addition to the pharmaceutically acceptable diluents, vehicles and other additives mentioned before, such other addenda as colorants, corrigents, and so on.

In addition to the above-mentioned unit dosage forms such as tablets, capsules, coated tablets, ampules, etc., the pharmaceutical compositions according to the present invention may be provided as contained in multiple dose containers or drug delivery systems.

Furthermore, depending upon dosage form and other conditions, the pharmaceutical compositions may contain the terpene amino alcohol generally in a concentration of 0.01 to 50 weight percent and preferably in a concentration of 0.1 to 20 weight percent.

The following examples are further illustrative of the present invention. It should be understood that the invention is not limited to these examples.

Example of Synthesis 1

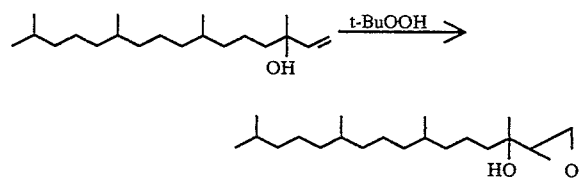

A three-necked flask of 2-liter capacity, fitted with a stirrer, reflux-condenser and thermometer, was charged with 463.6 g (1.57 moles) of isophytol, 221.8 g (1.72 moles) of a 70% (by weight) aqueous solution of t-butyl hydroperoxide and 710 mg of vanadium pentoxide and the reaction was conducted at 90° C. for 6 hours. Then, 350.4 g of a 14% (by weight) aqueous solution of sodium sulfite was added and the mixture was stirred at room temperature for 30 minutes. The reaction mixture was transferred to a separatory funnel. The upper layer was mixed with the same volume of 1N aqueous sodium hydroxide solution and stirred at room temperature and, then, extracted with n-hexane. The extract was washed with the same volume of water 3 times and the n-hexane was distilled off to give 467.0 g of 1,2-epoxy-3,7,11,15-tetramethylhexadecan-3-ol. Yield 96%.

Mass spectrum (m/z): 312(M+)

The above reaction and separation procedures were repeated except that linalool, 3,7-dimethyl-1-octen-3-ol or 3,7,11-trimethyl-1-dodecen-3-ol was used in lieu of isophytol. The results are shown in Table 5.

TABLE 5

| Starting compound | Product compound | Yield (%) | Mass spectrum |
|---|---|---|---|
| | | 45 | 170 (M+) |
| | | 83 | 172 (M+) |

TABLE 5-continued

| Starting compound | Product compound | Yield (%) | Mass spectrum |
|---|---|---|---|
| 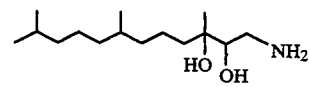 | | 87 | 242 (M+) |

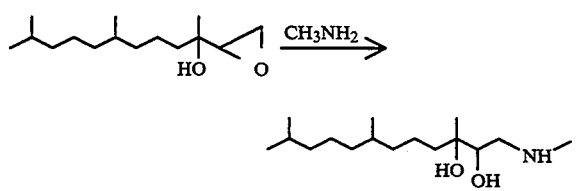

An autoclave was charged with 10 g of 1,2-epoxy-3,7,11-trimethyl-3-dodecanol and 12 g of a 50% aqueous solution of dimethylamine and the mixture was heated at 110° C. with stirring for 4 hours. Then, the reaction mixture was distilled under reduced pressure to give 9.9 g (yield 83%) of 1-(dimethylamino)-3,7,11-trimethyl-2,3-dodecanediol [Compound (16)]. The physical constants of Compound (16) are as follows.

Boiling point: 137° C./0.5 mm Hg
Mass spectrum (m/z): 287(M+)
$^1$H - NMR spectrum (90 MHz) δHMS CDCl$_3$: 0.83 (d, J=7Hz, 9H), 0.95~1.70 (m, 17H) 2.0 5~2.62 (m, 2H), 2.26 (s, 6 H), 3.4 3 (dd, J=5 & 9Hz, 1H), 3.4~3.8 (broad, 2H)

Example of Synthesis 2

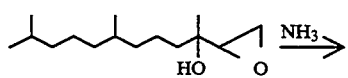

An autoclave was charged with 20 g of 1,2-epoxy-3,7,11-trimethyl-3-dodecanol and 70 ml of a 30% methanolic solution of methylamine and the mixture was heated at 110 ° C. with stirring for 4 hours. Then, the reaction mixture was distilled under reduced pressure to give 11.6 g (yield 51%) of 1-methylamino-3,7,11-trimethyl-2,3-dodecanediol [Compound (12)]. The physical constants of Compound (12) are as follows.

Boiling point: 133° C./0.2 mm Hg
Mass spectrum (m/z): 273 (M+)
$^1$H -NMR spectrum (90 MHz) δHMS CDCl$_3$: 0.81 (d, J=7 Hz, 9H), 0.90~1.70 (m, 17H), 2.38(s, 3H), 2.56~2.73(m, 2 H), 3.22 (broad s, 3H), 3.33~3.53 (m, 1H)

Example of Synthesis 3

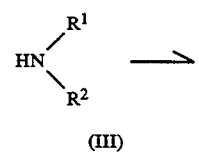

-continued

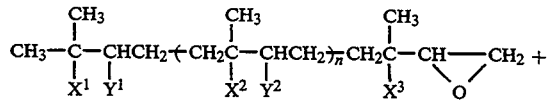

An autoclave was charged with 24.2 g of 1,2-epoxy-3,7,11-trimethyl-3-dodecanol and 10 ml of 28% aqueous ammonia and the mixture was heated at 100° C. with stirring for 6 hours. Then, the reaction mixture was distilled under reduced pressure and the residue was subjected to silica gel column chromatography (elution with 95% ethanol-5% triethylamine) to give 7.8 g (yield 30%) of 1-amino-3,7,11-trimethyl-2,3-dodecanediol [Compound (11)]. The physical constants of Compound (11) are as follows.

Mass spectrum (m/z): 259(M+)
$^1$H-NMR spectrum (90 MHz) δHMS CDCl$_3$: 0.82 (d, J=7Hz, 9H), 0.90~1.70 (m, 17H), 2.50~2.90 (m, 2H), 2.90~3.15 (broad, 4H), 3.15~3.50 (m, 1H)

Examples of Synthesis 4 to 17

$$CH_3-\underset{\underset{Y^1}{X^1}}{\overset{\overset{CH_3}{|}}{C}}-CHCH_2(CH_2\underset{\underset{Y^2}{X^2}}{\overset{\overset{CH_3}{|}}{C}}-CHCH_2)_{\overline{n}}CH_2\underset{X^3}{\overset{\overset{CH_3}{|}}{C}}-CH\diagdown\diagup CH_2 +$$

(II-1)

$$HN\diagdown\overset{R^1}{\underset{R^2}{\diagup}} \longrightarrow$$

(III)

$$CH_3-\underset{\underset{Y^1}{X^1}}{\overset{\overset{CH_3}{|}}{C}}-CHCH_2(CH_2\underset{\underset{Y^2}{X^2}}{\overset{\overset{CH_3}{|}}{C}}-CHCH_2)_{\overline{n}}CH_2\underset{X^3}{\overset{\overset{CH_3}{|}}{C}}-\underset{OH}{CH}CH_2N\diagdown\overset{R^1}{\underset{R^2}{\diagup}}$$

(I-11)

In the combinations shown in Table 6-1, an epoxyterpene (II-1) was reacted with an organic amino compound (III) in the same manner as Example of Synthesis 3. After completion of the reaction, the low-boiling fraction was distilled off and the residue was worked up as indicated in Table 6-1 to give the corresponding terpene amino alcohol of general formula (I-11). The yields and physical constants are shown in Table 6-2.

TABLE 6-1

| Example of Synthesis | Epoxyterpene (II-1) | Organic amino compound (III) | Separation procedure |
|---|---|---|---|
| 4 | 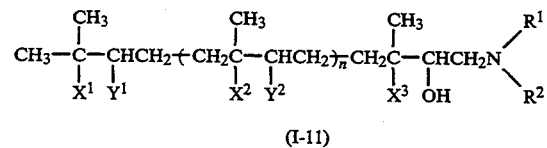 | NH$_3$ | Silica gel column chromatography |

TABLE 6-1-continued

| Example of Synthesis | Epoxyterpene (II-1) | Organic amino compound (III) | Separation procedure |
|---|---|---|---|
| 5 | (structure: HO, O) | $CH_3NH_2$ | Distillation under reduced pressure (96° C./0.25 mmHg) |
| 6 | (structure: HO, O) | $NH_3$ | Silica gel column chromatography |
| 7 | (structure: HO, O) | $CH_3NH_2$ | Distillation under reduced pressure (163° C./0.2 mmHg) |
| 8 | (structure: HO, O) | $(CH_3)_2NH$ | Distillation under reduced pressure (153° C./0.2 mmHg) |
| 9 | (structure: HO, O) | $(C_2H_5)_2NH$ | Distillation under reduced pressure (159° C./0.2 mmHg) |
| 10 | (structure: HO, O) | $(n\text{-}C_4H_9)_2NH$ | Distillation under reduced pressure (192° C./0.2 mmHg) |
| 11 | (structure: HO, O) | $NH_3$ | Silica gel column chromatography |
| 12 | (structure: HO, O) | $CH_3NH_2$ | Silica gel column chromatography |
| 13 | (structure: HO, O) | $(CH_3)_2NH$ | Distillation under reduced pressure (98.5° C./0.5 mmHg) |
| 14 | (structure: HO, O) | $C_2H_5NH_2$ | Distillation under reduced pressure (104° C./0.2 mmHg) |
| 15 | (structure: HO, O) | $n\text{-}C_3H_7NH_2$ | Silica gel column chromatography |
| 16 | (structure: HO, O) | $(C_2H_5)_2NH$ | Silica gel column chromatography |
| 17 | (structure: HO, O) | $n\text{-}C_4H_9NH_2$ | Silica gel column chromatography |

TABLE 6-2

| Example of Synthesis | Product | Yield (%) | Mass spectrum (m/z) | $^1$H-NMR spectrum (90 MHz) $\delta_{HMS}^{CDCl_3}$ |
|---|---|---|---|---|
| 4 | (structure: HO, OH, $NH_2$) [Compound (7)] | 41 | 189 (M$^+$) | 0.80(d, J=7Hz, 6H), 0.91~1.62(m, 10H), 2.5~2.9(m, 2H), 3.2~3.8(broad, 5H) |

TABLE 6-2-continued

| Example of Synthesis | Product | Yield (%) | Mass spectrum (m/z) | $^1$H-NMR spectrum (90 MHz) $\delta_{HMS}^{CDCl_3}$ |
|---|---|---|---|---|
| 5 | [Compound (8)] | 53 | 203 (M$^+$) | 0.81(d, J=7Hz, 6H), 1.12(s, 3H) 0.9~1.7(m, 7H), 2.37(s, 3H), 2.56~2.74(m, 2H, 2.87(broad s, 3H), 3.3~3.5(m, 1H) |
| 6 | [Compound (30)] | 35 | 329 (M$^+$) | 0.81(d, J=7Hz, 12H), 0.9~1.7(m, 24H), 2.5~2.8(m, 2H), 3.2~3.7(broad, 5H) |
| 7 | [Compound (31)] | 55 | 343 (M$^+$) | 0.80(d, J=7Hz, 12H), 0.9~1.7(m, 24H), 2.37(s, 3H), 2.57~2.73(m, 2H), 3.3~3.6(broad, 4H) |
| 8 | [Compound (32)] | 73 | 357 (M$^+$) | 0.80(d, J=7Hz, 12H), 0.9~1.67(m, 24H), 2.23(s, 6H), 2.33~2.60(m, 2H), 3.0~3.4(broad, 2H), 3.40(dd, J=4Hz and 9Hz, 1H) |
| 9 | [Compound (33)] | 69 | 385 (M$^+$) | 0.81(d, J=7Hz, 12H), 0.7~1.7(m, 30H), 2.25~2.75(m, 6H), 3.0~3.5(m, 3H) |
| 10 | [Compound (34)] | 77 | 441 (M$^+$) | 0.80(d, J=7Hz, 12H), 0.7~1.7(m, 38H), 2.2~2.65(m, 6H), 2.9~3.3(broad, 2H), 3.36(dd, J=5Hz and 9Hz, 1H) |
| 11 | [Compound 43)] | 40 | 187 (M$^+$) | 0.9~1.5(m, 5H); 1.55, 1.62(each s, 6H); 1.75~2.2(m, 2H); 2.6~3.2(m, 2H); 3.2~3.9(broad, 5H); 4.9~5.2(m, 1H) |
| 12 | [Compound 44)] | 52 | 201 (M$^+$) | 1.06(s, 3H); 1.3~1.5(m, 2H); 1.57, 1.63(each s, 6H); 1.8~2.3(m, 2H); 2.39(s, 3H); 2.55~2.75(m, 2H); 3.17(broad s, 3H); 3.33~3.55(m, 1H); 4.95~5.20(m, 1H) |
| 13 | [Compound 45)] | 63 | 215 (M$^+$) | 1.03(s, 3H); 1.3~1.5(m, 2H), 1.8~2.65(m, 4H), 2.26(s, 6H), 3.1~3.6(m, 3H), 4.95~5.20(m, 1H) |
| 14 | [Compound (46)] | 49 | 215 (M$^+$) | 1.09(s, 3H); 1.09(t, J=7Hz, 3H); 1.3~1.5(m, 2H); 1.59, 1.64(each s, 6H); 1.8~2.25(m, 2H); 2.62(q, J=7Hz, 2H); 2.6~2.8(m, 2H); 2.97(broad s, 3H); 3.33~3.50(m, 1H); 4.97~5.23(m, 1H) |
| 15 | [Compound (47)] | 51 | 229 (M$^+$) | 0.7~1.5(m, 10H); 1.58, 1.64(each s, 6H); 1.8~2.25(m, 2H); 2.4~3.1(m, 7H); 3.30~3.53(m, 1H); 4.95~5.23(m, 1H) |

TABLE 6-2-continued

| Example of Synthesis | Product | Yield (%) | Mass spectrum (m/z) | $^1$H-NMR spectrum (90 MHz) $\delta_{HMS}{}^{CDCl_3}$ |
|---|---|---|---|---|
| 16 | [Compound (48)] | 67 | 243 (M$^+$) | 0.9~1.2(m, 9H); 1.3~1.5(m, 2H); 1.59, 1.64(each s, 6H); 1.8~2.25(m, 2H); 2.4~2.7(m, 6H); 3.30~3.53(m, 1H); 4.95~5.23(m, 1H) |
| 17 | [Compound (49)] | 47 | 243 (M$^+$) | 0.7~1.5(m, 12H); 1.58, 1.64(each s, 6H); 1.8~2.25(m, 2H); 2.4~2.8(m, 4H); 2.8~3.2(broad, 3H); 3.33~3.50(m, 1H); 4.95~5.23(m, 1H) |

Example of Synthesis 18

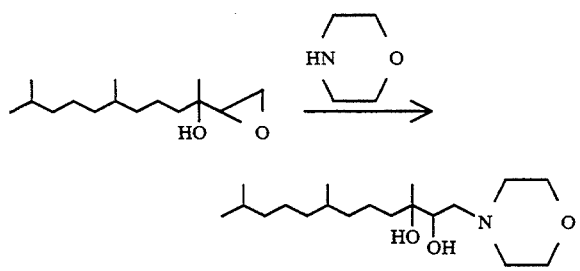

A flask was filled with 10 g of 1,2-epoxy-3,7,11-trimethyl-3-dodecanol and 10 ml of morpholine and the mixture was refluxed at 129° C. for 5 hours. Then, the morpholine was removed by distillation and the residue was distilled under reduced pressure to give 10.0 g (yield 74%) of 3,7,11-trimethyl-1-morpholino-2,3-dodecanediol [Compound (17)]. The physical constants of Compound (17) are as follows.

Boiling point: 165° C./0.2 mm Hg
Mass spectrum (m/z): 329 (M$^+$)
$^1$H- NMR spectrum (90 MHz) $\delta$CDCl$_3$: 0.83 (d, J=7Hz, 9H), 1.0~1.7 (m, 17H), 2.20~2.75 (m, 6H), 3.15~3.55 (broad, 2H), 3.4~3.6 (m, 1H), 3.6~3.8 (m, 4H)

Example of Synthesis 19

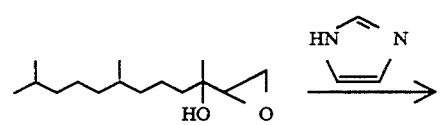

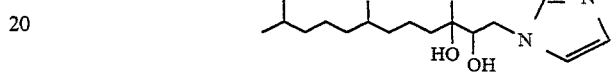

A flask was filled with 12 g of 1,2-epoxy-3,7,11-trimethyl-3-dodecanol and 10 g of imidazole and the mixture was heated at 170° C. for 5 hours. Then, the reaction mixture was distilled under reduced pressure to give 11.7 g (yield 71%) of 1-(1H-imidazol-1-yl)-3,7,11-trimethyl-2,3-dodecanediol [Compound (21)]. The physical constants of Compound (21) are as follows.

Boiling point: 205° C./0.04 mm Hg
Mass spectrum (m/z): 310 (M$^+$)
$^1$H-NMR spectrum (90 HHz) $\delta$HMS CDCl$_3$: 0.82 (d, J=7Hz, 9H), 0.9~1.8 (m, 17 H), 3.45~3.7 (m, 5H), 6.82 (d, J=6Hz, 2H), 7.27 (s, 1 H)

Example of Synthesis 20

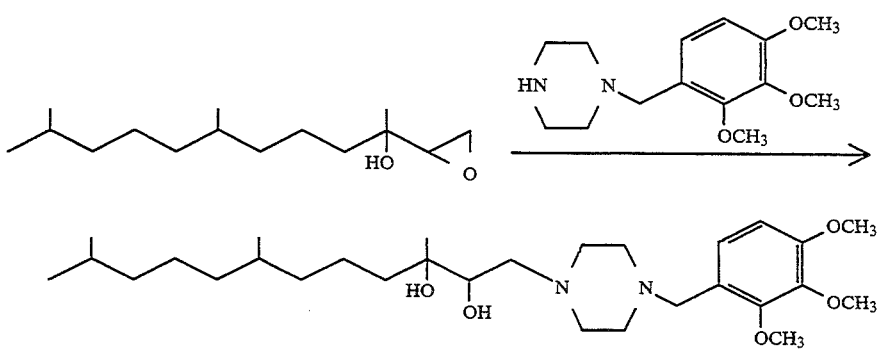

A flask was filled with 7 g of 1,2-epoxy-3,7,11-trimethyl-3-dodecanol, 9.23 g of 4-[(2,3,4-trimethoxyphenyl)-methyl]piperazine and 20 ml of toluene and the mixture was refluxed at 110° C. for 2 hours. Then, the toluene was removed by distillation and the residue was subjected to silica gel column chromatography (elution with 98% ethanol-2% triethylamine) to give 13.9 g (yield 95%) of 3,7,11-trimethyl-1-[4-[(2,3,4-trimethoxyphenyl)methyl]piperazin-1-yl]-2,3-dodecanediol [Compound (18)]. The physical constants of Compound (18) are as follows.

FD-mass spectrum: 508 (M$^+$)
$^1$H-NMR spectrum (90 MHz) $\delta$HMS CDCl$_3$: 0.82 (d, J=7Hz, 9H); 0.96~1.67 (m, 17 H); 2.3~2.75 (m, 10 H); 3.25~3.6 (m, 5H); 3.77, 3.82 (each s, 9H); 6.58 (d, J=8Hz, 1 H); 6.95 (d, J=8Hz, 1H)

Example of Synthesis 21

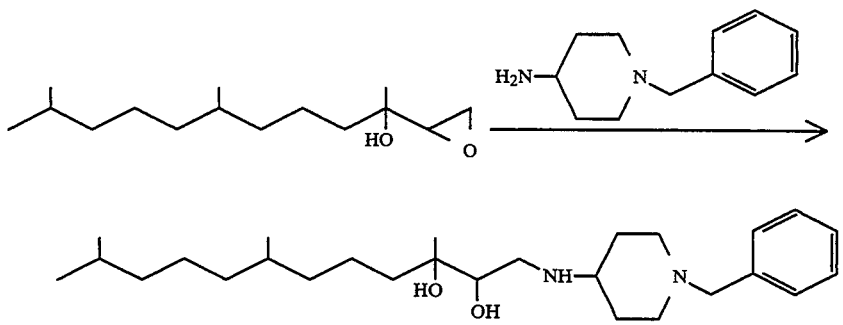

A flask was filled with 9 g of 1,2-epoxy-3,7,11-trimethyl-3-dodecanol, 22 g of 4-amino-1-(phenylmethyl)-piperidine and 30 ml of xylene and the mixture was refluxed at 140° C. for 10 hours. Then, the xylene was removed by distillation and the residue was subjected to silica gel column chromatography (elution with 95% ethanol-5% triethylamine) to give 2.5 g (yield 16%) of 1-[(1-benzylpiperidin-4-yl) amino ]-3,7-11- trimethyl-2,3-dodecanediol [Compound (40)]. The physical constants of Compound (40) are as follows.

FD-mass spectrum: 420(M+)

$^1$H-NMR spectrum (90 MHz) δHMS CDCl$_3$: 0.81 (d, J=7Hz, 9H), 0.9~1.65 (m, 17 H), 1.65~2.2 (m, 4H), 2.2~3.0 (m, 6H), 3.07 (broad, 3H), 3.3~3.5 (m, 2H), 3.42 (s, 2H), 7.27 (s, 5H)

Examples of Synthesis 22 to 34

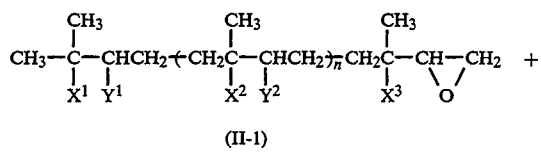

(II-1)

-continued

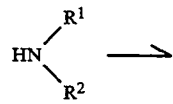

(III)

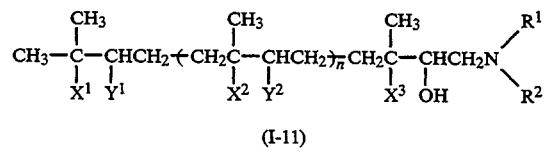

(I-11)

In the combinations shown in Table 7-1, an epoxyterpene (II-1) was reacted with an organic amino compound (III) under heating. After confirming the disappearance of the epoxyterpene, the low-boiling fraction was distilled off and the residue was worked up as indicated in Table 7-1 to give the corresponding terpene amino alcohol of general formula (I-11). The yields and physical constants are shown in Table 7-2.

TABLE 7-1

| Example of Synthesis | Epoxyterpene (II-1) | Terpene amino compound (III) | Separation procedure |
|---|---|---|---|
| 22 | | (n-C$_4$H$_9$)$_2$NH | Silica gel column chromatography |
| 23 | | | Silica gel column chromatography |
| 24 | | | Silica gel column chromatography |
| 25 | | | Silica gel column chromatography |
| 26 | | | Silica gel column chromatography |

TABLE 7-1-continued

| Example of Synthesis | Epoxyterpene (II-1) | Terpene amino compound (III) | Separation procedure |
|---|---|---|---|
| 27 | (epoxyterpene with HO groups) | HO-CH₂CH₂-NH-CH₃ | Distillation under reduced pressure (153.5° C./0.55 mmHg) |
| 28 | (epoxyterpene with HO) | (n-C₄H₉)₂NH | Silica gel column chromatography |
| 29 | (epoxyterpene with HO) | HO-CH₂CH₂-NH₂ | Silica gel column chromatography |
| 30 | (longer epoxyterpene with HO) | (n-C₄H₉)₂NH | Distillation under reduced pressure (166° C./0.4 mmHg) |
| 31 | (longer epoxyterpene with HO) | morpholine-N-CH₂CH₂CH₂-NH₂ | Silica gel column chromatography |
| 32 | (longer epoxyterpene with HO) | pyrrolidine (NH) | Distillation under reduced pressure (100° C./0.02 mmHg) |
| 33 | (longer epoxyterpene with HO) | piperidine (NH) | Distillation under reduced pressure (100° C./0.05 mmHg) |
| 34 | morpholine-N-CH₂CH₂CH₂-NH₂ | HO-CH₂CH₂-NH-CH₃ | Silica gel column chromatography |

TABLE 7-2

| Example of Synthesis | Product | Yield (%) | Mass spectrum (m/z) | ¹H-NMR spectrum (90 MHz) $\delta_{HMS}^{CDCl_3}$ |
|---|---|---|---|---|
| 22 | [Compound (1)] | 72 | 299 (M⁺) | 0.75~1.55(m, 16H), 1.03(s, 3H), 1.59, 1.65(each s, 6H), 1.83~2.20(m, 2H), 2.20~2.67(m, 6H), 3.1~3.6(m, 3H), 4.97~5.23(m, 1H) |
| 23 | [Compound (2)] | 68 | 277 (M⁺) | 1.14(s, 3H), 1.40~1.75(m, 2H), 1.60, 1.66(each s, 6H), 1.9~2.25(m, 2H), 2.25~2.60(broad, 2H), 2.91(s, 3H) 3.20~3.35(m, 2H), 3.60~3.85(m, 1H), 4.98~5.23(m, 1H), 6.65~6.93(m, 3H), 7.10~7.35(m, 2H) |
| 24 | [Compound (3)] | 75 | 241 (M⁺) | 1.06(s, 3H), 1.33~1.85(m, 6H), 1.59, 1.65(each s, 6H), 1.85~2.20(m, 2H), 2.2~2.9(m, 6H), 3.37~3.75(m, 3H), 4.97~5.23(m, 1H) |

TABLE 7-2-continued

| Example of Synthesis | Product | Yield (%) | Mass spectrum (m/z) | $^1$H-NMR spectrum (90 MHz) $\delta_{HMS}^{CDCl_3}$ |
|---|---|---|---|---|
| 25 | 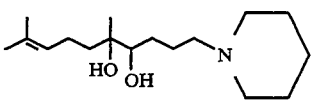<br>[Compound (4)] | 81 | 255 (M$^+$) | 1.03(s, 3H), 1.3~1.8(m, 8H), 1.59, 1.64(each s, 6H), 1.80~2.15(m, 2H), 2.15~2.8(m, 6H), 3.15~3.6(m, 3H), 4.97~5.23(m, 1H) |
| 26 | 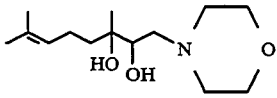<br>[Compound (5)] | 84 | 257 (M$^+$) | 1.05(s, 3H), 1.33~1.53(m, 2H), 1.59, 1.65(each s, 6H), 1.80~2.22(m, 2H), 2.22~2.9(m, 6H), 3.1~3.4(broad, 2H), 3.4~3.8(m, 4H), 4.97~5.23(m, 1H) |
| 27 | 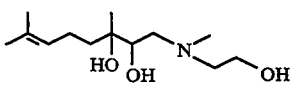<br>[Compound (6)] | 71 | 245 (M$^+$) | 1.03(s, 3H), 1.30~1.53(m, 2H), 1.57, 1.63(each s, 6H), 1.85~2.20(m, 2H), 2.29(s, 3H), 2.35~2.80(m, 6H), 3.4~3.7(m, 5H), 4.97~5.23(m, 1H) |
| 28 | 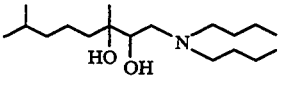<br>[Compound (9)] | 83 | 301 (M$^+$) | 0.83(d, J=8Hz, 6H), 0.7~1.0(m, 6H), 1.0~1.7(m, 15H), 1.27(s, 3H), 2.15~2.7(m, 8H), 3.37(dd, J=5Hz and 9Hz, 1H) |
| 29 | 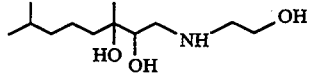<br>[Compound (10)] | 44 | 233 (M$^+$) | 0.82(d, J=7Hz, 6H), 0.93~1.70(m, 7H), 1.31(s, 3H), 2.5~2.9(m, 4H), 3.3~3.85(m, 7H) |
| 30 | 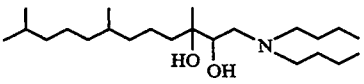<br>[Compound (13)] | 77 | 371 (M$^+$) | 0.81(d, J=7Hz, 9H), 0.7~1.0(m, 6H), 1.0~1.7(m, 25H), 2.2~2.7(m, 6H), 2.9~3.6(broad, 2H), 3.37(dd, J=5Hz and 9Hz, 1H) |
| 31 | 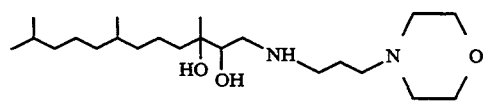<br>[Compound (22)] | 39 | 386 (M$^+$) | 0.81(d, J=7Hz, 9H), 1.34(s, 3H), 0.9~1.8(m, 16H), 2.25~2.50(m, 6H), 2.5~2.8(m, 4H), 2.8~3.13(broad, 3H), 3.3~3.5(m, 1H), 3.57~3.80(m, 4H) |
| 32 | 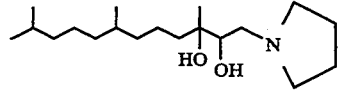<br>[Compound (38)] | 94 | 313 (M$^+$) | 0.82(d, J=7Hz, 9H), 0.9~1.6(m, 17H), 1.6~1.9(m, 4H), 2.2~2.9(m, 6H), 3.37~3.53(m, 1H), 3.5~3.8(broad, 2H) |
| 33 | 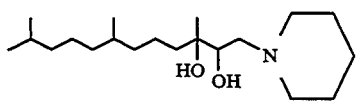<br>[Compound (39)] | 89 | 327 (M$^+$) | 0.82(d, J=7Hz, 9H), 0.9~1.7(m, 23H), 2.15~2.7(m, 6H), 3.1~3.7(m, 3H) |
| 34 | 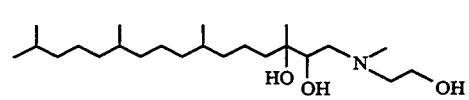<br>[Compound (35)] | 75 | 387 (M$^+$) | 0.80(d, J=7Hz, 12H), 0.9~1.7(m, 24H), 2.26(s, 3H), 2.2~2.8(m, 4H), 3.29(broad s, 3H), 3.3~3.5(m, 1H), 3.59(t, J=5Hz, 2H) |

Examples of Synthesis 35 to 43

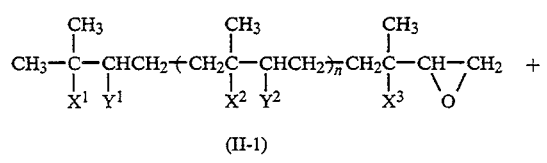

(II-1)

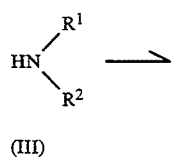

(III)

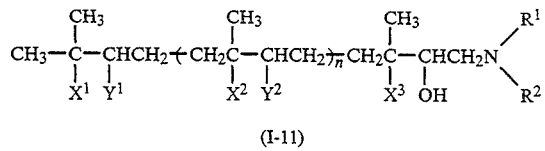

(I-11)

In the combinations shown in Table 8-1, an epoxyterpene (II-1) was reacted with an organic amino compound (III) in the same manner as Example of Synthesis 21. After completion of the reaction, the xylene was distilled off and the residue was worked up as indicated in Table 8-1 to give the corresponding terpene amino alcohol of general formula (I-11). The yields and physical constants are shown in Table 8-2.

TABLE 8-1

| Example of Synthesis | Epoxyterpene (II-1) | Terpene amino compound (III) | Separation procedure |
|---|---|---|---|
| 35 | [epoxyterpene structure with HO and O] | HO–CH₂CH₂–NH₂ | Silica gel column chromatography |
| 36 | [epoxyterpene structure with HO and O] | HO–C₆H₄–NH₂ (4-aminophenol) | Silica gel column chromatography |
| 37 | [epoxyterpene structure with HO and O] | 4-aminopyridine | Silica gel column chromatography |
| 38 | [epoxyterpene structure with HO and O] | 5-aminoquinoline | Silica gel column chromatography |
| 39 | [epoxyterpene structure with HO and O] | 1-(diphenylmethyl)piperazine | Silica gel column chromatography |
| 40 | [epoxyterpene structure with HO and O] | benzimidazolone (2,3-dihydro-1H-benzimidazol-2-one) | Silica gel column chromatography |
| 41 | [epoxyterpene structure with HO and O] | thiomorpholine | Silica gel column chromatography |
| 42 | [epoxyterpene structure with HO and O] | 3-(aminomethyl)pyridine | Silica gel column chromatography |

TABLE 8-1-continued

| Example of Synthesis | Epoxyterpene (II-1) | Terpene amino compound (III) | Separation procedure |
| --- | --- | --- | --- |
| 43 | (structure: long chain with HO and epoxide) | (structure: piperazine with 2-methoxyphenyl and NH) | Silica gel column chromatography |

TABLE 8-2

| Example of Synthesis | Product | Yield (%) | FD-Mass spectrum |
| --- | --- | --- | --- |
| 35 | [Compound (14)] | 42 | 303 (M$^+$) |
| 36 | [Compound (19)] | 26 | 351 (M$^+$) |
| 37 | [Compound (20)] | 37 | 336 (M$^+$) |
| 38 | [Compound (23)] | 31 | 386 (M$^+$) |
| 39 | [Compound (24)] | 43 | 494 (M$^+$) |
| 40 | [Compound (25)] | 40 | 376 (M$^+$) |
| 41 | [Compound (26)] | 63 | 345 (M$^+$) |

TABLE 8-2-continued

| Example of Synthesis | Product | Yield (%) | FD-Mass spectrum |
|---|---|---|---|
| 42 | 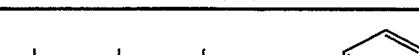<br>[Compound (41)] | 48 | 350 (M+) |
| 43 | 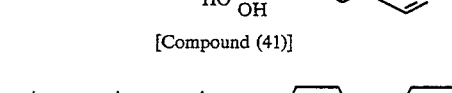<br>[Compound (43)] | 55 | 434 (M+) |

Example of Synthesis 44

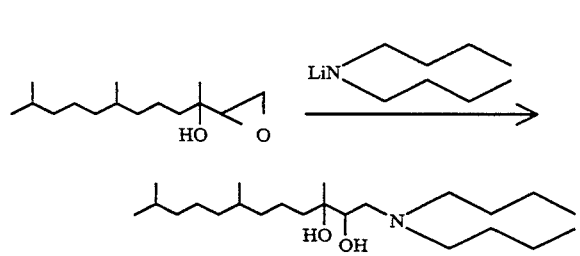

Under nitrogen atmosphere, 65 ml of n-butyllithium (1.6M/hexane) was added dropwise to a solution of 12.9 g of di-n-butylamine in 30 ml of tetrahydrofuran at −78° C. and, after completion of addition, the mixture was stirred at 0° C. for 30 minutes. A solution of 12.1 of 1,2-epoxy-3,7,11-trimethyl-3-dodecanol in 20 ml of tetrahydrofuran was added dropwise slowly at 0° C. to the above solution. The mixture was stirred at room temperature for 2 hours, after which it was poured into ice-water and extracted with diethyl ether. The extract was washed with water and dried over anhydrous magnesium sulfate. The solvent was then distilled off and the residue was distilled under reduced pressure to give 15.8 g (yield 85%) of 1-dibutylamino-3,7,11-trimethyl-2,3-dodecanediol [Compound (13)].

Example of Synthesis 45

A solution of 10 g of 1-(methylamino)-3,7,11-trimethyl-2,3-dedecanediol and 8.7 g of pyridine in 100 ml of dichloroethane was cooled to −30° C. and 7.2 g of nicotinoyl chloride hydrochloride was added gradually to the above solution. The mixture was stirred at room temperature for 3 hours. Thereafter, the reaction mixture was poured into water and extracted with dichloroethane. The organic layer was washed with aqueous sodium hydrogen carbonate and dried over anhydrous magnesium sulfate. The solvent was then distilled off and the residue was subjected to silica gel column chromatography (elution with ethanol) to give 12.0 g (yield 93%) of N-methyl-N-(3,7,11-trimethyl-2,3-hydroxydodecyl) nicotinamide [Compound (15). The physical constants of Compound (15) are as follows.

FD-Mass spectrum: 378 (M+)

$^1$H -NMR spectrum (90 MHz) δHMS CDCl$_3$: 0.83 (d, J=7Hz, 9H), 0.9~1.7 (m, 17H), 2.33 (s, 3H), 2.3~2.7 (m, 2H), 3.3~3.7 (m, 1H), 7.25~7.50 (m, 1H), 8.25~8.45 (m, 1H), 8.70~8.85 (m, 1H), 9.20~9.30 (m, 1H)

Example of Synthesis 46

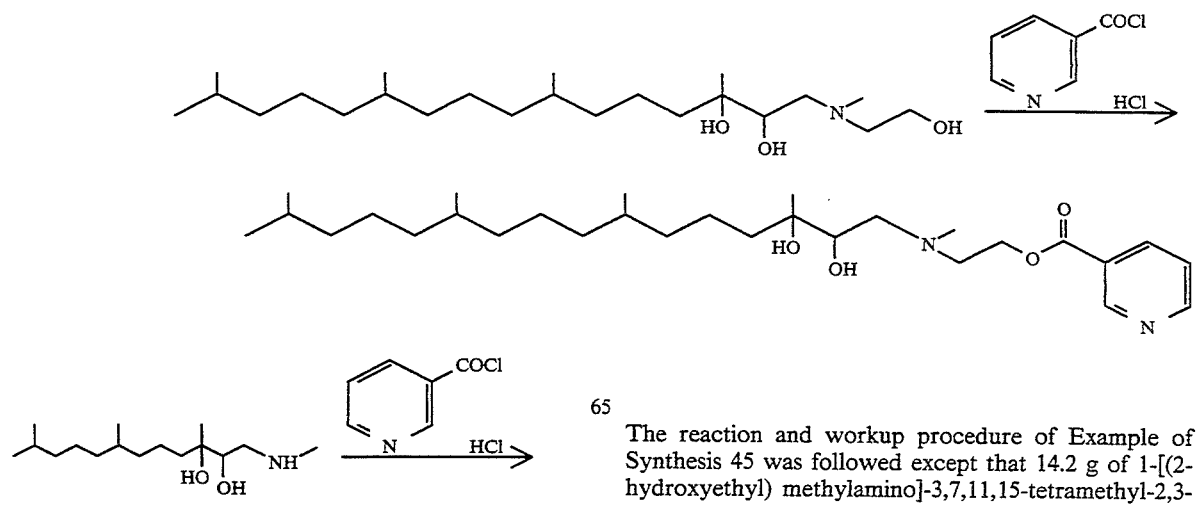

The reaction and workup procedure of Example of Synthesis 45 was followed except that 14.2 g of 1-[(2-hydroxyethyl) methylamino]-3,7,11,15-tetramethyl-2,3- hexadecanediol was used in lieu of 10 g of 1-(methylamino) -3,7,11-trimethyl-2,3-dodecanedioi to give 14.4 g (yield 80%) of 2-[N-(2,3-dihydroxy-3,7,11,15-tetramethyl hexadecyl)-N-methylamino]ethyl nicotinate [Compound (36)].

FD-Mass spectrum: 492 (M+)

Example of Synthesis 47

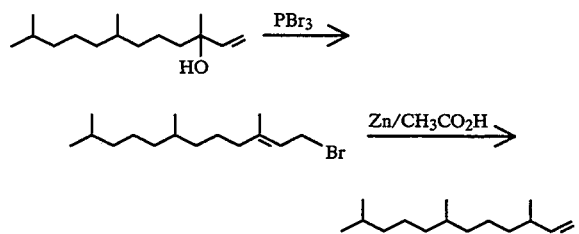

In 300 ml of hexane were dissolved 50 g of 3,7,11-trimethyl-1-dodecen-3-ol and 0.87 g of pyridine, and 30.8 g of phosphorus tribromide was added dropwise to the solution at 0° to −10° C. After 2 hours of stirring at 0° C., the reaction mixture was poured into water and extracted with hexane. The hexane layer was successively washed with aqueous sodium hydrogen carbonate and aqueous sodium chloride and dried over anhydrous magnesium sulfate. The solvent was distilled off to give 62.5 g of crude 1-bromo-3,7,11-trimethyl-2-dodecene. To a suspension of 14.2 g of zinc in 26 ml of acetic acid was added dropwise 62.5 g of the crude 1-bromo-3,7,11-trimethyl-2-dodecene and the mixture was stirred at room temperature for 1 hour. Thereafter, the zinc was filtered off and the filtrate was poured into water and extracted with hexane. The hexane layer was washed with aqueous sodium hydrogen carbonate and aqueous sodium chloride in that order and dried over anhydrous sodium sulfate. The solvent was then distilled off and the residue was further distilled under reduced pressure to give 10.6 g (yield 25%) of 3,7,11-trimethyl-1-dodecene. The physical constants of the compound are as follows.

Boiling point: 114° C./0.35 mm Hg
Mass spectrum (m/z): 210(M+)

1H-NMR spectrum (90 MHz) δHMS CDCl3: 0.80 (d, J=7Hz, 9H), 0.91 (d, J=7Hz, 3H), 1.0~1.75 (m, 14H), 1.75~2.3 (m, 1H), 4.75~5.03 (m, 2H), 5.35~5.87 (m, 1H)

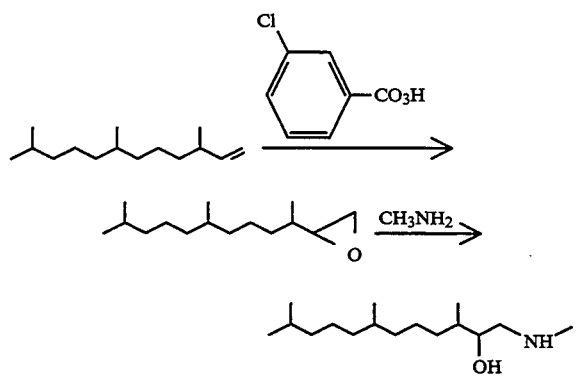

To a solution of 9.6 g of 3,7,11-trimethyl-1-dodecene in 200 ml of methylene chloride was added 10.8 g of meta-chloroperbenzoic acid at room temperature, and the mixture was stirred at the same temperature for 6 hours. Thereafter, the reaction mixture was filtered and the filtrate was washed successively with aqueous sodium thiosulfate, aqueous sodium hydrogen carbonate and aqueous sodium chloride and dried over anhydrous magnesium sulfate. The solvent was distilled off and the residue was distilled under reduced pressure to give 6.8 g (yield 59%) of 1,2-epoxy-3,7,11-trimethyldodecane. The physical constants of the compound are as follows.

Boiling point: 94° C./0.4 mm Hg
Mass spectrum (m/z): 226(M+)

An autoclave was charged with 3.4 g of 1,2-epoxy-3,7,11-trimethyldodecane and 5 g of methylamine (40% in methanol) and the mixture was heated at 110° C. with stirring for 3 hours. Thereafter, the reaction mixture was distilled under reduced pressure to give 2.0 g (yield 51%) of 1-methylamino-3,7,11-trimethyl-2-dodecanol [Compound (28)]. The physical constants of Compound (28) are as follows.

Boiling point: 125° C./0.1 mmHg
Mass spectrum (m/z): 257(M+)

1H-NMR spectrum (90 MHz) δHMS CDCl3: 0.83 (d, J=7Hz, 12H), 1.0~1.7 (m, 15H), 2.40 (s, 3H), 2.4~2.6 (m, 2 H), 3.23 (broad s, 2H), 3.30~3.65 (m, 1 H)

Example of Synthesis 48

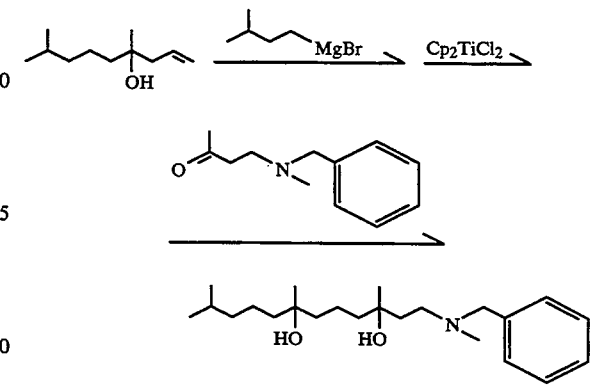

To an isobutylmagnesium bromide solution prepared from 14.6 g of magnesium, 68.5 g of isobutyl bromide and 500 ml of diethyl ether was added dropwise under ice-cooling a solution of 34 g of 4,8-dimethyl-1-nonen-4-ol in 100 ml of diethyl ether and, after completion of the addition, the mixture was stirred at room temperature for 20 minutes. To the solution was added 2.5 g of titanocene dichloride at room temperature and the mixture was stirred at the same temperature for 18 hours, followed by dropwise addition of 38.2 g of 4-(benzylmethylamino)-2-butanone under ice-cooling. The mixture was stirred at the same temperature for 30 minutes, poured into saturated aqueous ammonium chloride and extracted with diethyl ether. The ether was distilled off and chloroform was added to the residue. The mixture was successively washed with saturated aqueous sodium chloride and a small amount of aqueous sodium hydrogen carbonate and dried over anhydrous sodium sulfate. The chloroform was distilled off and the residue was subjected to silica gel column chromatography (elution with 95% methylene chloride-5% triethylamine) to give 7.5 g (yield 11%) of 1-(methylbenzylamino)-3,7,11-trimethyl-3,7-dodecanediol [Compound (29)]. The physical constants of Compound (29) are as follows.

Mass spectrum (m/z): 363 (M+)

¹H-NMR spectrum (90 MHz) δHMS CDCl₃: 0.86 (d, J=7 Hz, 6H); 1.12, 1.17 (each s, 6H); 1.0~1.7 (m, 15H); 2.0~2.25 (m, 3H); 2.5~2.75 (m, 2H); 3.3~3.55 (m, 4H); 7.29 (broad s, 5H)

Example of Synthesis 49

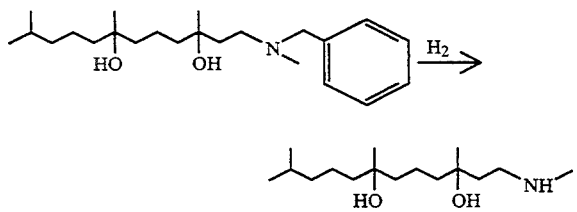

An autoclave was charged with 7.5 g of 1-(methylbenzylamino)-3,7,11-trimethyl-3,7-dodecanediol, 0.75 g of palladium-on-carbon and 30 ml of ethanol and the reaction was allowed to proceed at 40° C. under hydrogen pressure (10 atm.). Thereafter, the ethanol was distilled off and the residue was subjected to silica gel column chromatography (elution with 95% ethanol-5% triethylamine) to give 4.3 g (yield 77%) of 1-(methylamino)-3,7,11-trimethyl-3,7-dodecanediol [Compound (27)]. The physical constants of Compound (27) are as follows.

Mass spectrum (m/z): 273 (M+)

¹H-NMR spectrum (90MHz) δHMS CDCl₃: 0.83 (d, J=7Hz, 6H), 1.0~1.8 (m, 21H), 2.36(s, 3H), 2.76(t, J=7Hz, 2H), 3.0~3.4 (broad, 3H)

Example of Synthesis 50

4-(benzylmethylamino)-2-butanone to give 5.0 g (yield 10%) of 1-(methylbenzylamino)-3,7,11-trimethyl-3,7,11-dodecanetriol [Compound (37)].

Mass spectrum (m/z): 379 (M+)

Example of Synthesis 51

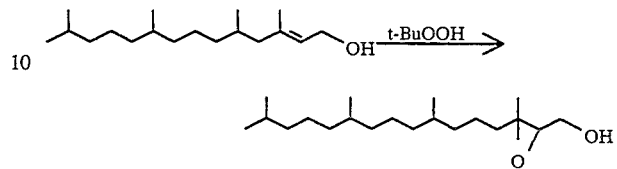

A three-necked flask of 2-liter capacity, fitted with a stirrer, reflux-condenser and thermometer, was charged with 463.6 g (1.57 moles) of phytol, 221.8 g (1.72 moles) of a 70% (by weight) aqueous solution of t-butyl hydroperoxide and 710 mg of vanadium pentoxide and the reaction was conducted at 90° C. for 6 hours. Then, 350.4 g of a 14% (by weight) aqueous solution of sodium sulfite was added and the mixture was stirred at room temperature for 30 minutes. The reaction mixture was transferred to a separatory funnel. The upper layer was mixed with the same volume of 1N aqueous sodium hydroxide solution and stirred at room temperature and, then, extracted with n-hexane. The extract was washed with the same volume of water 3 times and the n-hexane was distilled off to give 467.0 g (yield 96%) of 2,3-epoxy-3,7,11,15-tetramethylhexadecan-1-ol.

Mass spectrum (m/z): 312 (M+)

The above reaction and separation procedures were

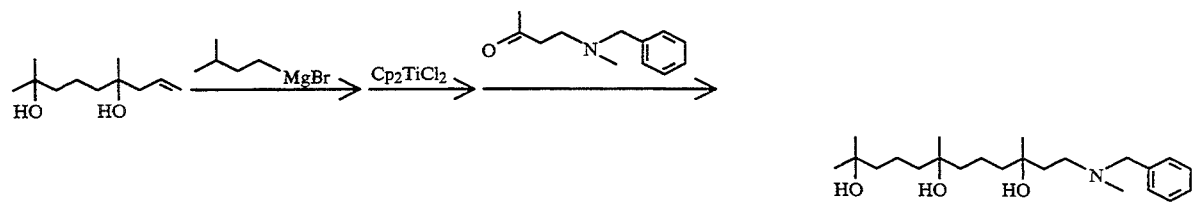

The reaction and workup procedure of Example of Synthesis 48 was followed except that 25 g of 4,8-dimethyl-1-nonene-4,8-diol was used in lieu of 34 g of 4,8-dimethyl-1-nonen-4-ol and 25.5 g of 4-(benzylmethylamino)-2-butanone was used in lieu of 38.2 g of repeated except that geraniol, 3,7-dimethyl-2-octen-1-ol or 3,7,11-trimethyl-2-dodecen-1-ol was used in lieu of phytol. The results are set forth in Table 9.

TABLE 9

| Starting compound | Product | Yield (%) | Mass spectrum |
|---|---|---|---|
|  |  | 54 | 170 (M+) |
|  |  | 79 | 172 (M+) |
|  |  | 85 | 242 (M+) |
|  |  |  |  |

A solution of 17.2 g of 2,3-epoxy-3,7-dimethyl-1-octanol, 15.0 g of (2-hydroxyethyl)methylamine and 20 ml of toluene was refluxed for 4 hours. After the reaction was completed, the reaction mixture was distilled under reduced pressure to give 21.0 g (yield 85%) of 2-[(2-hydroxyethyl )methylamino ]-3,7-dimethyl-1,3-octanediol [Compound (60)]. The physical constants of Compound (60) are as follows.

Boiling point: 154° C./0.2 mmHg
Mass spectrum (m/z): 247 (M+)
$^1$H-NMR spectrum (90 MHz) δHMS CDCl$_3$: 0.82 (d, J=7Hz, 6H) , 1.13 (s, 6H), 0.8~1.7 (m, 7H), 2.48 (s, 3H), 2.5~2.75(m, 1H), 2.8~3.0 (m, 2H), 3.35~4.1 (m, 7H)

Example of Synthesis 52

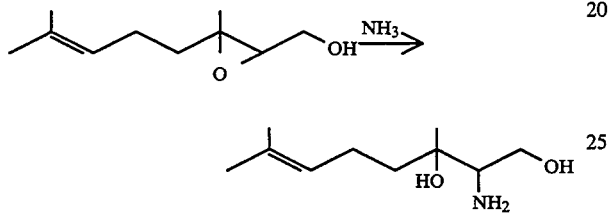

An autoclave was charged with 17.0 g of 2,3-epoxy-3,7-dimethyl-6-octen-1-ol and 10 ml of aqueous ammonia (28%) and the mixture was heated at 100° C. with stirring for 6 hours. Thereafter, the low-boiling fraction was distilled off and the residue was subjected to silica gel column chromatography (elution with 95% ethanol-5% triethylamine) to give 7.9 g (yield 42%) of 2-amino-3,7-dimethyl-6-octene-1,3-diol [Compound (50)]. The physical constants of Compound (50) are as follows.

Mass spectrum (m/z ): 187 (M+)
$^1$H-NMR spectrum(90 MHz) δHMS CDCl$_3$: 1.27 (s, 3 H), 1.59, 1.60 (each s, 6 H), 1.3~1.7 (m, 2H); 1.9~2.25 (m, 2H); 2.4~2.6 (broad, 1H); 2.92 (dd, J=5Hz & 6Hz , 1 H); 3.5~3.9 (m, 2H); 4.9~5.2 (m, 1 H)

Examples of Synthesis 53 to 71

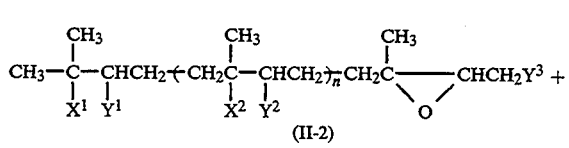

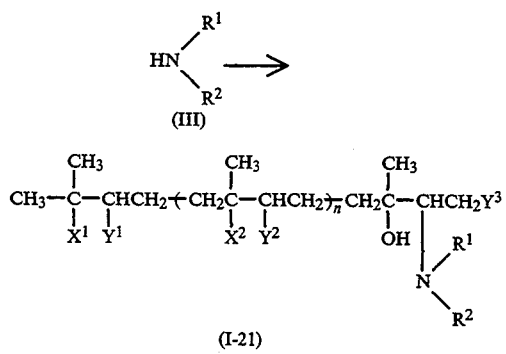

In the combinations shown in Table 10, an epoxyterpene (II-2) was reacted with an organic amino compound (III) in the same manner as Examples of Synthesis 51 and 52. The same after-treatment as described in said Examples gave the corresponding terpene amino alcohols of general formula (I-21). The yields and physical constants are shown in Table 10.

TABLE 10

| Example of Synthesis | Epoxyterpene (II-2) | Organic amino compound (III) | Product | Yield (%) | Mass spectrum (m/z) |
|---|---|---|---|---|---|
| 53 | (epoxy terpene with OH) | HN(CH₃)₂ | [Compound (51)] | 51 | 215 (M⁺) |
| 54 | (epoxy terpene with OH) | H₂N-propyl | [Compound (52)] | 47 | 231 (M⁺) |
| 55 | (epoxy terpene with OH) | HN(butyl)₂ | [Compound (53)] | 46 | 299 (M⁺) |
| 56 | (epoxy terpene with OH) | pyrrolidine (HN) | [Compound (54)] | 39 | 241 (M⁺) |
| 57 | (epoxy terpene with OH) | piperidine (HN) | [Compound (55)] | 38 | 255 (M⁺) |

TABLE 10-continued

| Example of Synthesis | Epoxyterpene (II-2) | Organic amino compound (III) | Product | Yield (%) | Mass spectrum (m/z) |
|---|---|---|---|---|---|
| 58 | (structure with OH and epoxide) | morpholine (HN with O ring) | [Compound (56)] | 36 | 257 (M+) |
| 59 | (structure with OH and epoxide) | HN—CH₂CH₂—OH | [Compound (57)] | 41 | 245 (M+) |
| 60 | (structure with OH and epoxide) | NH₃ | [Compound (58)] | 77 | 189 (M+) |
| 61 | (structure with OH and epoxide) | HN—(butyl) | [Compound (59)] | 81 | 301 (M+) |
| 62 | (epoxide structure) | NH₃ | [Compound (61)] | 76 | 243 (M+) |
| 63 | (structure with OH and epoxide) | NH₂— | [Compound (62)] | 83 | 273 (M+) |

TABLE 10-continued

| Example of Synthesis | Epoxyterpene (II-2) | Organic amino compound (III) | Product | Yield (%) | Mass spectrum (m/z) |
|---|---|---|---|---|---|
| 64 | | | [Compound (63)] | 87 | 420 (M+) |
| 65 | | | [Compound (64)] | 90 | 310 (M+) |
| 66 | | | [Compound (65)] | 73 | 508 (M+) |
| 67 | | | [Compound (67)] | 80 | 303 (M+) |
| 68 | | | [Compound (68)] | 69 | 345 (M+) |

TABLE 10-continued

| Example of Synthesis | Epoxyterpene (II-2) | Organic amino compound (III) | Product | Yield (%) | Mass spectrum (m/z) |
|---|---|---|---|---|---|
| 69 | | | [Compound (69)] | 74 | 386 (M+) |
| 70 | | | [Compound (72)] | 87 | 357 (M+) |
| 71 | | | [Compound (73)] | 85 | 387 (M+) |

Example of Synthesis 72

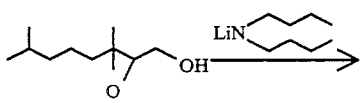

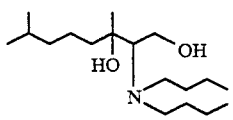

Under nitrogen atmosphere, 65 ml of n-butyllithium (1.6M in hexane) was added dropwise to a solution of 2.9 g of di-n-butylamine in 30 ml of tetrahydrofuran at −78° C. and after completion of addition, the mixture was stirred at 0° C. for 30 minutes. To this solution was added a solution of 8.6 g of 2,3-epoxy-3,7-dimethyl-1-octanol in 20 ml of tetrahydrofuran slowly in portions at 0° C. The mixture was then stirred at room temperature for 2 hours, after which it was poured into ice-water and extracted with diethyl ether. The extract was washed with water and after drying over anhydrous magnesium sulfate, the solvent was distilled off. The residue was further distilled under reduced pressure to give 12 g of 2-(dibutylamino)-3,7-dimethyl-1,3-octanediol Compound (59)]. Yield 80%.

Example of. Synthesis 73

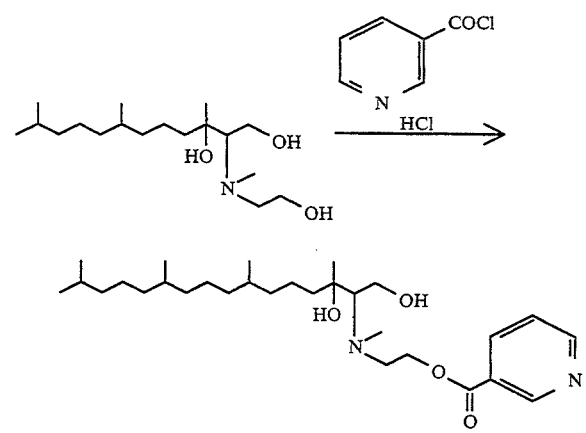

In 100 ml of dichloroethane were dissolved 10 g of 2-(methylamino)-3,7,11-trimethyl-1,3-dodecanediol and 8.7 g of pyridine and the solution was cooled to −30° C. To this solution was added 7.2 g of nicotinoyl chloride hydrochloride gradually and the mixture was stirred at room temperature for 3 hours. After the reaction was completed, the reaction mixture was poured into water and extracted with dichloroethane. The organic layer was washed with aqueous sodium hydrogen carbonate and after drying over anhydrous magnesium sulfate, the solvent was distilled off. Finally, the residue was subjected to silica gel column chromatography (elution with ethanol) to give 12.0 g of N-methyl-N-(1,3-dihydroxy-3,7,11-trimethyldodecan-2-yl)nicotinamide [Compound (66)]. Yield 93%.

FD-Mass spectrum: 378(M+)

Example of Synthesis 74

The same reaction and workup procedure as Example of Synthesis 73 was followed except that 14.2 g of 2-[(2-hydroxyethyl)methylamino]-3,7,11,15-tetramethyl-1,3-hexadecanediol was used in lieu of 10 g of 2-(methylamino)-3,7,11-trimethyl-1,3-dodecanediol to obtain 12.6 g of 2-[(2-nicotinoyloxyethyl)methylamino]-3,7,11,15-tetramethyl-1,3-hexadecanediol [Compound (74)]. Yield 70%.

FD-Mass spectrum: 492(M+)

Example of Synthesis 75

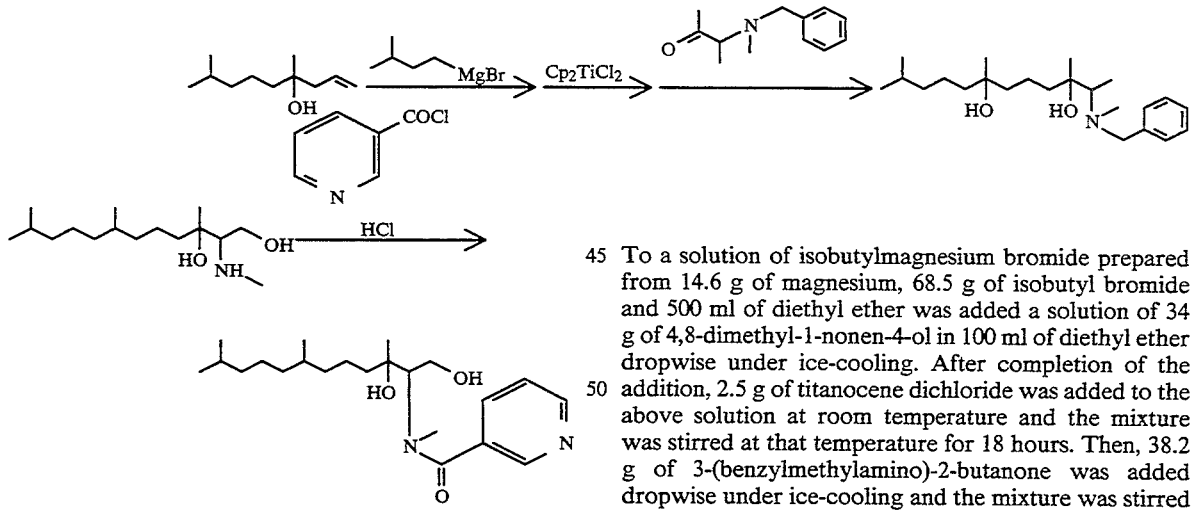

To a solution of isobutylmagnesium bromide prepared from 14.6 g of magnesium, 68.5 g of isobutyl bromide and 500 ml of diethyl ether was added a solution of 34 g of 4,8-dimethyl-1-nonen-4-ol in 100 ml of diethyl ether dropwise under ice-cooling. After completion of the addition, 2.5 g of titanocene dichloride was added to the above solution at room temperature and the mixture was stirred at that temperature for 18 hours. Then, 38.2 g of 3-(benzylmethylamino)-2-butanone was added dropwise under ice-cooling and the mixture was stirred at that temperature for 30 minutes. The reaction mixture was poured into a saturated aqueous solution of ammonium chloride and extracted with diethyl ether. The ether was distilled off, and after addition of chloroform, the residue was washed with a saturated aqueous solution of sodium chloride and a small amount of aqueous sodium hydrogen carbonate. After drying over anhydrous sodium sulfate, the chloroform was distilled off and the residue was subjected to silica gel column chromatography (elution with 95% methylene chloride-5% triethylamine) to give 11.3 g of 2-(benzylmethylamino)-3,7,11-trimethyl-3,7-dodecanediol [Compound (71)]. Yield 17%.

Mass spectrum (m/z): 363(M+)

Example of Synthesis 76

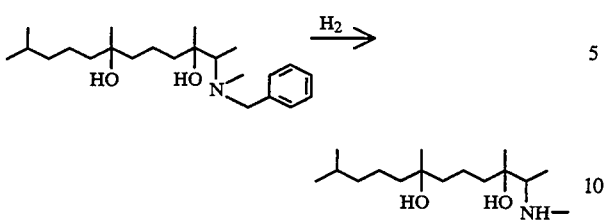

An autoclave was charged with 7.5 g of 2-(benzylmethylamino)-3,7,11-trimethyl-3,7-dodecanediol, 0.75 g of palladium-on-carbon and 30 ml of ethanol, and the reaction was conducted at 40° C. under hydrogen pressure (10 atm). After completion of the reaction, the ethanol was distilled off and the residue was subjected to silica gel column chromatography (elution with 95% ethanol-5% triethylamine) to give 3.6 g of 2-(methylamino)-3,7,11-trimethyl-3,7-dodecanediol [Compound (70)]. Yield 65%.

Mass spectrum (m/z): 273 (M+)

Pharmaceutical examples using Compound (14), Compound (36) and Compound (53), which are among the object compounds of the present invention, as active components are given below.

| Pharmaceutical Example 1 Capsules | |
|---|---|
| Compound (14) | 5 g |
| Microcrystalline cellulose | 80 g |
| Corn starch | 20 g |
| Lactose | 22 g |
| Polyvinylpyrrolidone | 3 g |
| Total | 130 g |
| Compound (36) | 5 g |
| Microcrystalline cellulose | 80 g |
| Corn starch | 20 g |
| Lactose | 22 g |
| Polyvinylpyrrolidone | 3 g |
| Total | 130 g |
| Compound (53) | 5 g |
| Microcrystalline cellulose | 80 g |
| Corn starch | 20 g |
| Lactose | 22 g |
| Polyvinylpyrrolidone | 3 g |
| Total | 130 g |

The above batches of components were respectively granulated and filled into 1,000 hard gelatin capsules each by the established pharmaceutical procedure. Each capsule contained 5 mg of Compound (14), Compound (36) or Compound (53).

| Pharmaceutical Example 2 Powders | |
|---|---|
| Compound (14) | 50 g |
| Microcrystalline cellulose | 400 g |
| Corn starch | 550 g |
| Total | 1,000 g |
| Compound (36) | 50 g |
| Microcrystalline cellulose | 400 g |
| Corn starch | 550 g |
| Total | 1,000 g |
| Compound (53) | 50 g |
| Microcrystalline cellulose | 400 g |
| Corn starch | 550 g |
| Total | 1,000 g |

Compound (14) was dissolved in acetone, adsorbed on microcrystalline cellulose and dried. It was then blended with the corn starch to provide a powder in the routine manner. This powder was a 20-fold dilution of Compound (14). By the same procedure as above, a 1/20 powder of Compound (36) and a 1/20 powder of Compound (53) were manufactured.

| Pharmaceutical Example 3 Tablets | |
|---|---|
| Compound (14) | 5 g |
| Corn starch | 10 g |
| Lactose | 20 g |
| Carboxymethylcellulose calcium | 10 g |
| Microcrystalline cellulose | 40 g |
| Polyvinylpyrrolidone | 5 g |
| Talc | 10 g |
| Total | 100 g |
| Compound (36) | 5 g |
| Corn starch | 10 g |
| Lactose | 20 g |
| Carboxymethylcellulose calcium | 10 g |
| Microcrystalline cellulose | 40 g |
| Polyvinylpyrrolidone | 5 g |
| Talc | 10 g |
| Total | 100 g |
| Compound (53) | 5 g |
| Corn starch | 10 g |
| Lactose | 20 g |
| Carboxymethylcellulose calcium | 10 g |
| Microcrystalline cellulose | 40 g |
| Polyvinylpyrrolidone | 5 g |
| Talc | 10 g |
| Total | 100 g |

Compound (14) was dissolved in acetone, adsorbed on microcrystalline cellulose and dried. It was then blended with corn starch, lactose and carboxymethylcellulose Ca, followed by addition of an aqueous solution of polyvinylpyrrolidone as a binder. The whole mixture was granulated in the routine manner. To the granules was added talc as a lubricant and after blending, the mixture was tableted at the rate of 100 mg per tablet. The tablets each contained 5 mg of Compound (14).

By the same procedure as above, tablets each containing 100 mg of Compound (36) and tablets each containing 100 mg of Compound (53) were manufactured. Each of these tablets contained 5 mg of Compound (36) or Compound (53).

| Pharmaceutical Example 4 Injections | |
|---|---|
| Compound (14) | 10 g |
| Nikkol HCO-60 (Nikko Chemical) | 37 g |
| Sesame oil | 2 g |
| Sodium chloride | 9 g |
| Propylene glycol | 40 g |
| Phosphate buffer (0.1M, pH 6.0) | 100 g |
| Distilled water to make | 1,000 g |
| Compound (36) | 10 g |
| Nikkol HCO-60 (Nikko Chemical) | 37 g |
| Sesame oil | 2 g |
| Sodium chloride | 9 g |
| Propylene glycol | 40 g |
| Phosphate buffer (0.1M, pH 6.0) | 100 g |
| Distilled water to make | 1,000 g |
| Compound (53) | 10 g |
| Nikkol HCO-60 (Nikko Chemical) | 37 g |
| Sesame oil | 2 g |
| Sodium chloride | 9 g |
| Propylene glycol | 40 g |
| Phosphate buffer (0.1M, pH 6.0) | 100 g |
| Distilled water to make | 1,000 g |

Compound (14), Nikkol HCO-60, sesame oil and a half of the quantity of propylene glycol were mixed and heated at about 80° C. To the resulting solution were added phosphate buffer and a solution of sodium chloride and propylene glycol in distilled water prewarmed to about 80° C. to make a total of 1,000 ml. This aqueous solution was filled into 2 ml ampules and, after sealing by fusion, heat-sterilized.

This parenteral preparation contained 20 mg of Compound (14) in each ampule.

By the same procedure as above, parenteral products containing 20 mg of Compound (36) or Compound (53) per ampule were manufactured.

What is claimed is:

1. A terpene amino alcohol of the formula

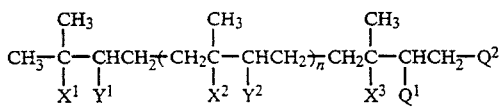

wherein $X^1$ is a hydrogen atom or a hydroxyl group and $Y^1$ is a hydrogen atom, or $X^1$ and $Y^1$ taken together represent a bond; $X^2$ is a hydrogen atom or a hydroxyl group and $Y^2$ is a hydrogen atom, or $X^2$ and $Y^2$ taken together represent a bond; $Q^1$ and $Q^2$ are such that either one is $Y^3$ with the other group being

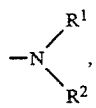

and $X^3$ is a hydrogen atom or a hydroxyl group; $Y^3$ is a hydroxyl group when $X^3$ is a hydrogen atom, or $Y^3$ is a hydrogen atom or a hydroxyl group when $X^3$ is a hydroxyl group; $R^1$ and $R^2$ taken together with the adjacent nitrogen atom form a pyrrolidinyl ring; and n is an integer of 0 to 2; or a pharmacologically acceptable ester or salt thereof.

2. The compound according to claim 1, which is 3,7-dimethyl-1-(1-pyrrolidinyl)-6-octene-2,3-diol.

3. The compound according to claim 1, which is 1-(1-pyrrolidinyl)-3,7,11-trimethyl-2,3-dodecanediol.

4. The compound according to claim 1, which is 3,7-dimethyl-2-(1-pyrrolidinyl)-6-octene-1,3-diol.

5. A pharmaceutical composition for the prevention or treatment of allergic diseases or disorders of cerebral function which comprises an amount, effective for the prevention or treatment of said allergic diseases of disorders of cerebral function, of a terpene amino alcohol of the formula

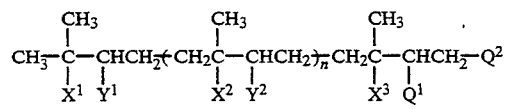

wherein $X^1$ is a hydrogen atom or a hydroxyl group and $Y^1$ is a hydrogen atom, or $X^1$ and $Y^1$ taken together represent a bond; $X^2$ is a hydrogen atom or a hydroxyl group and $Y^2$ is a hydrogen atom, or $X^2$ and $Y^2$ taken together represent a bond; $Q^1$ and $Q^2$ are such that either one is $Y^3$ with the other group being

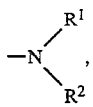

and $X^3$ is a hydrogen atom or a hydroxyl group; $Y^3$ is a hydroxyl group when $X^3$ is a hydrogen atom, or $Y^3$ is a hydrogen atom or a hydroxyl group when $X^3$ is a hydroxyl group; $R^1$ and $R^2$ taken together with the adjacent nitrogen atom form a pyrrolidinyl ring; and n is an integer of 0 to 2; or a pharmacologically acceptable ester or salt thereof; and a pharmaceutically acceptable diluent or carrier therefor.

6. The composition according to claim 5, wherein the terpene amino alcohol is 3,7-dimethyl-1-(1-pyrrolidinyl)-6-octene-2,3-diol.

7. The composition according to claim 5, wherein the terpene amino alcohol is 1-(1-pyrrolidinyl)-3,7,11-trimethyl-2,3-dodecanediol.

8. The composition according to claim 5, wherein the terpene amino alcohol is 3,7-dimethyl-2-(1-pyrrolidinyl)-6-octene-1,3-diol.

9. A method for preventing or treating allergic diseases or disorders of cerebral function which comprises administering to an animal in need thereof an effective amount for the prevention or treatment of said allergic diseases or disorders of cerebral function of a terpene amino alcohol of the formula

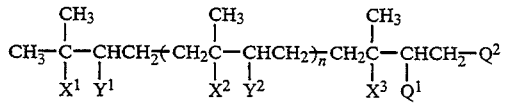

wherein $X^1$ is a hydrogen atom or a hydroxyl group and $Y^1$ is a hydrogen atom, or $X^1$ and $Y^1$ taken together represent a bond; $X^2$ is a hydrogen atom or a hydroxyl group and $Y^2$ is a hydrogen atom, or $X^2$ and $Y^2$ taken together represent a bond; $Q^1$ and $Q^2$ are such that either one is $Y^3$ with the other group being

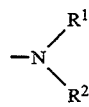

and $X^3$ is a hydrogen atom or a hydroxyl group; $Y^3$ is a hydroxyl group when $X^3$ is a hydrogen atom, or $Y^3$ is a hydrogen atom or a hydroxyl group when $X^3$ is a hydroxyl group; $R^1$ and $R^2$ taken together with the adjacent nitrogen atom form a pyrrolidinyl ring; and n is an integer of 0 to 2; or a pharmacologically acceptable ester or salt thereof.

10. The method according to claim 9, wherein the terpene amino alcohol is 3,7-dimethyl-1-(1-pyrrolidinyl)-6-octene-2,3-diol.

11. The method according to claim 9, wherein the terpene amino alcohol is 1-(1-pyrrolidinyl)-3,7,11-trimethyl-2,3-dodecanediol.

12. The method according to claim 9, wherein the terpene amino alcohol is 3,7-dimethyl-2-(1-pyrrolidinyl)-6-octene-1,3-diol.

* * * * *